US012224046B2

United States Patent
Embree et al.

(10) Patent No.: US 12,224,046 B2
(45) Date of Patent: *Feb. 11, 2025

(54) SYSTEM FOR EMR VITALS CHARTING

(71) Applicant: Hill-Rom Services, Inc., Batesville, IN (US)

(72) Inventors: Stephen Embree, Chapel Hill, NC (US); Douglas A. Seim, Okeana, OH (US); Frederick Collin Davidson, Apex, NC (US); Britten J. Pipher, Raleigh, NC (US); Kenzi Mudge, Raleigh, NC (US); Bradley T. Smith, Raleigh, NC (US); Steven D. Baker, Beaverton, OR (US); Eric Agdeppa, Cincinnati, OH (US); Pamela Wells, Hixson, TN (US); Laura A. Hassey, Raleigh, NC (US); Andrew S. Robinson, Durham, NC (US); Thomas A. Myers, Syracuse, NY (US)

(73) Assignee: Hill-Rom Services, Inc., Batesville, IN (US)

( * ) Notice: Subject to any disclaimer, the term of this patent is extended or adjusted under 35 U.S.C. 154(b) by 268 days.

This patent is subject to a terminal disclaimer.

(21) Appl. No.: 17/852,762

(22) Filed: Jun. 29, 2022

(65) Prior Publication Data

US 2022/0328151 A1     Oct. 13, 2022

Related U.S. Application Data

(63) Continuation of application No. 16/535,303, filed on Aug. 8, 2019, now Pat. No. 11,404,149.

(Continued)

(51) Int. Cl.
    *G06K 9/00*     (2022.01)
    *G10L 15/26*     (2006.01)
    (Continued)

(52) U.S. Cl.
    CPC .............. *G16H 10/60* (2018.01); *G10L 15/26* (2013.01); *G16H 15/00* (2018.01); *G06F 40/00* (2020.01);
    (Continued)

(58) Field of Classification Search
    CPC ........ G16H 10/60; G16H 15/00; G16H 40/20; G16H 40/60; G16H 40/67; G10L 15/26;
    (Continued)

(56) References Cited

U.S. PATENT DOCUMENTS

| | | |
|---|---|---|
| 5,561,412 A | 10/1996 | Novak et al. |
| 5,699,038 A | 12/1997 | Ulrich et al. |

(Continued)

FOREIGN PATENT DOCUMENTS

| | | |
|---|---|---|
| CN | 107945841 A | 4/2018 |
| WO | 2017/083353 | 5/2017 |
| WO | 2019/179888 | 9/2019 |

OTHER PUBLICATIONS

Second Office Action issued by the Chinese Patent Office for Chinese Patent Application No. 2019108048162 on Aug. 28, 2023, and its English translation (12 pages).

(Continued)

*Primary Examiner* — Maroun P Kanaan
(74) *Attorney, Agent, or Firm* — Barnes & Thornburg LLP

(57) ABSTRACT

A charting system is provided for use in a healthcare facility having a network. The charting system includes a microphone to receive voice inputs from a caregiver. A vital sign monitor obtains a vital sign from a patient and displays it. The system includes a communication device having a voice-to-text module that includes a processor coupled to the microphone. The processor operates a voice-to-text algorithm that converts the vital sign into text in response to the (Continued)

caregiver dictating the vital sign into the microphone. The processor initiates transmission of the vital sign to an EMR computer via the network after conversion of the at least one vital sign to text.

20 Claims, 5 Drawing Sheets

Related U.S. Application Data

(60) Provisional application No. 62/724,752, filed on Aug. 30, 2018.

(51) Int. Cl.
*G16H 10/60* (2018.01)
*G16H 15/00* (2018.01)
*G06F 40/00* (2020.01)
*G06Q 10/06* (2023.01)
*G06Q 10/10* (2023.01)
*G16H 40/20* (2018.01)

(52) U.S. Cl.
CPC ............. *G06Q 10/06* (2013.01); *G06Q 10/10* (2013.01); *G16H 40/20* (2018.01)

(58) Field of Classification Search
CPC ........ G06F 40/00; G06Q 10/06; G06Q 10/10; H04W 4/023; H04W 4/029; H04W 64/006
See application file for complete search history.

(56) References Cited

U.S. PATENT DOCUMENTS

| | | | |
|---|---|---|---|
| 5,715,548 A | 2/1998 | Weismiller et al. | |
| 5,838,223 A | 11/1998 | Gallant et al. | |
| 6,147,592 A | 11/2000 | Ulrich et al. | |
| 6,362,725 B1 | 3/2002 | Ulrich et al. | |
| 6,897,780 B2 | 5/2005 | Ulrich et al. | |
| 7,242,308 B2 | 7/2007 | Ulrich et al. | |
| 7,257,531 B2 | 8/2007 | Holub | |
| 7,296,312 B2 | 11/2007 | Menkedick et al. | |
| 7,319,386 B2 | 1/2008 | Collins, Jr. et al. | |
| 7,538,659 B2 | 5/2009 | Ulrich et al. | |
| 7,746,218 B2 | 6/2010 | Collins, Jr. et al. | |
| 7,849,400 B2 | 12/2010 | Ritter et al. | |
| 8,046,625 B2 | 10/2011 | Ferguson et al. | |
| 8,169,304 B2 | 5/2012 | Schuman, Sr. et al. | |
| 8,310,179 B2 | 11/2012 | Clough | |
| 8,384,256 B2 | 2/2013 | De Filippis | |
| 8,598,995 B2 | 12/2013 | Schuman et al. | |
| 9,236,046 B2 | 1/2016 | Watson et al. | |
| 10,074,364 B1 | 9/2018 | Wightman et al. | |
| 10,176,297 B2 | 1/2019 | Zerhusen et al. | |
| 10,249,386 B2 | 4/2019 | Blechman | |
| 10,347,255 B1 | 7/2019 | Paul et al. | |
| 10,417,385 B2 | 9/2019 | Kusen et al. | |
| 10,546,655 B2 * | 1/2020 | Owen | G16H 30/40 |
| 11,404,149 B2 | 8/2022 | Embree et al. | |
| 2004/0073363 A1 * | 4/2004 | Sanchez | G08B 21/0202 701/469 |
| 2006/0059012 A1 | 3/2006 | Thompson | |
| 2006/0288095 A1 | 12/2006 | Torok et al. | |
| 2007/0080801 A1 | 4/2007 | Weismiller et al. | |
| 2009/0138284 A1 | 5/2009 | Guadagna et al. | |
| 2009/0212925 A1 | 8/2009 | Schuman, Sr. et al. | |
| 2009/0212926 A1 | 8/2009 | Du et al. | |
| 2009/0217080 A1 | 8/2009 | Ferguson et al. | |
| 2012/0166225 A1 | 6/2012 | Albro et al. | |
| 2013/0172691 A1 | 7/2013 | Tran | |
| 2014/0266642 A1 | 9/2014 | Girardeau et al. | |
| 2014/0324477 A1 | 10/2014 | Oez | |
| 2014/0361909 A1 | 12/2014 | Stelfox et al. | |
| 2015/0033295 A1 | 1/2015 | Huster | |
| 2017/0323555 A1 | 11/2017 | Embree et al. | |
| 2018/0144097 A1 | 5/2018 | Moore | |
| 2018/0161225 A1 | 6/2018 | Zerhusen et al. | |
| 2019/0272145 A1 | 9/2019 | Sharma et al. | |
| 2020/0051689 A1 | 2/2020 | Hoernig | |
| 2020/0066402 A1 | 2/2020 | Bechtel et al. | |
| 2020/0066415 A1 * | 2/2020 | Hettig | G16H 50/30 |
| 2020/0075140 A1 | 3/2020 | Embree et al. | |

OTHER PUBLICATIONS

"Nurses turn to speech-recognition software to speed documentation," from Modern Health Care; Dec. 12, 2015; pages.

Communication pursuant to Article 94(3) EFC issued on May 12, 2023, issued in the European Patent Application No. 19192804.3; 7 pages.

Decision of Rejection issued in Chinese Patent Application No. 201910804816.2 on Jan. 12, 2024, and its English translation (11 pages).

Extended EP Search Report for European Patent Application No. 19192804.3 dated Jan. 30, 2020 (10 pages).

Conn, Joseph: "Nurses turn to speech-recognition software to speed documentation," Modern Healthcare, Dec. 12, 2015 (Dec. 12, 2015), XP055659586.

"Voice Recognition Based Advance Patient's Room Automation," by Tejaswiny Singh et al.; International Journal of Research in Engineering and Technology; vol. 4, Issue 6; Jun. 2015; pp. 308-310 (3 pages).

First Office Action issued by the Chinese Patent Office on Feb. 8, 2023, for Chinese Patent Application No. 2019108048162, and its English translation (15 pages).

\* cited by examiner

SYSTEM FOR EMR VITALS CHARTING

The present application is a continuation of U.S. application Ser. No. 16/535,303, filed Aug. 8, 2019, now U.S. Pat. No. 11,404,149, which claimed the benefit, under 35 U.S.C. § 119 (e), to U.S. Provisional Application No. 62/724,752, filed Aug. 30, 2018, each of which is hereby incorporated by reference herein in its entirety.

BACKGROUND

The present disclosure relates to healthcare information technology systems and particularly, to healthcare information technology systems having an electronic medical records (EMR) system and a real time location system (RTLS). More particularly, the present disclosure relates to charting medical information, such as vital signs information, of a patient into the patient's EMR.

Caregivers in healthcare facilities are required to chart patient vital signs data and other information into electronic medical records (EMR's) of their assigned patients. Typically, the caregivers type the data to be charted into each patient's EMR using an EMR computer. It takes time for caregivers to manually enter the required data using the EMR computer. The vital signs to be input into the EMR of the patients are usually sensed by one or more pieces of equipment within each patient's room. For example, vital signs such as blood pressure, heartrate, temperature, respiratory rate and the like are monitored by various pieces of equipment. Thus, before entering the vital signs data into the EMR's of patients, caregivers sometimes write down the vital signs data on a piece of paper and then refer back to the written information when typing the data into the EMR at the EMR computer. Writing down the vital signs information is an additional manual step that also takes time.

Caregivers sometimes also provide other clinical inputs or observations about their patients using the EMR computer. Patient complexion, bruising, rashes, pain level, and the like are examples of these other clinical inputs. Usually, but not always, these additional clinical inputs are not capable of being sensed with equipment but instead, require direct observation by the caregiver. It takes even more of the caregivers' time to manually type these clinical observations into the EMR's of patients using the EMR computer. Accordingly, caregivers would appreciate a system that eliminates or greatly reduces the amount of time required to manually type vital sign data and other clinical inputs into the EMR's of their patients.

SUMMARY

The present disclosure includes one or more of the features recited in the appended claims and/or the following features which, alone or in any combination, may comprise patentable subject matter.

According to the present disclosure, a charting system may be provided for use in a healthcare facility having a network. The charting system may include a microphone that may be configured to receive voice inputs from a caregiver and a vital sign monitor that may be configured to obtain at least one vital sign from a patient and to display the at least one vital sign. The system may further include a communication device that may have a voice-to-text module that may include a processor communicatively coupled to the microphone. The processor may operate a voice-to-text algorithm. An electronic medical record (EMR) computer may be communicatively coupled to the voice-to-text module. The voice-to-text algorithm may be configured to convert the at least one vital sign into text in response to the caregiver dictating the at least one vital sign into the microphone. The processor may be configured to initiate transmission of the at least one vital sign to the EMR computer via the network after conversion of the at least one vital sign to text.

In some embodiments, the communication device having the voice-to-text module may include one or more of the following: a patient bed that may be located in a patient room, a caregiver locating tag that may be worn by the caregiver, an audio station of a nurse call system, or a computer that may be located in the patient room. Optionally, the microphone also may be carried by the communication device. The voice-to-text algorithm also may be configured to convert other clinical inputs into text in response to the caregiver dictating the other clinical inputs into the microphone. The other clinical inputs may include, for example, information regarding one or more of the following: patient complexion, pain level of the patient, bruising of the patient, or any rashes on the patient.

It is contemplated by this disclosure that the voice-to-text algorithm may be configured to be activated by the caregiver prior to dictation. For example, the voice-to-text algorithm may be configured to be activated with a button. Alternatively or additionally, the voice-to-text algorithm may be configured to be activated in response to the caregiver speaking a keyword.

In some embodiments, the charting system further includes a locating system that may be coupled to the voice-to-text module. The locating system may include locating receivers that may be situated throughout the healthcare facility and a caregiver locating tag that may be worn by the caregiver. The caregiver locating tag may communicate with one or more of the locating receivers that may be in communicative proximity with the caregiver locating tag. The locating system further may include a locating server that may be communicatively coupled to the locating receivers. The locating server may be configured to notify the voice-to-text module that the caregiver has entered the patient room. Thus, the voice-to-text algorithm may be activated in response to the caregiver entering the patient room. Alternatively or additionally, the vital sign monitor may be activated in response to the caregiver entering the patient's room.

Optionally, the caregiver locating tag may include a plurality of buttons and each button of the plurality of buttons may be related to a respective caregiver activity. Furthermore, each button of the plurality of buttons may be selectable by the caregiver to convey information about the respective caregiver activity to the voice-to-text module. In some embodiments, the voice-to-text module may track a time that the caregiver selects each button of the plurality of buttons. The respective caregiver activity for at least one of the buttons of the plurality of buttons may include, for example, at least one of the following: completion of caregiver rounds, medication administration, completion of physical therapy, or taking of the at least one vital sign. The locating system may be operable to identify which caregiver has entered the patient room and the voice-to-text module may be configured to record which caregiver has entered the patient room in response to receipt of a message from the locating server.

In some embodiments, the charting system further may include a high accuracy locating system that may be communicatively coupled to the communication device having the voice-to-text module. The high accuracy locating system may include locating transceivers that may be situated throughout the healthcare facility and a caregiver locating tag that may be worn by the caregiver. The caregiver locating tag may communicate with one or more of the locating transceivers that may be in communicative proximity with the caregiver locating tag. The locating system further may include a locating server that may be communicatively coupled to the locating transceivers and that may be operable to determine a location of the caregiver locating tag in the healthcare facility within three feet or less of an actual location of the caregiver locating tag. The locating server may be configured to communicate a message to the voice-to-text module indicating that the caregiver is within three feet or less of the communication device.

It is contemplated by this disclosure that the plurality of transceivers may communicate via ultra-wideband (UWB) signals with the caregiver locating tag. In some embodiments, the location of the caregiver locating tag may be determined by the locating server using two way ranging and time difference of arrival (TDOA) techniques. The locating server may use signals from only a subset of the plurality of transceivers to determine the location of the caregiver locating tag. For example, the subset may be determined based on signal strength of signals between the caregiver locating tag and the plurality of transceivers. The subset may include at least three transceivers from the plurality of transceivers that may have highest signal strength values as compared to others of the plurality of transceivers.

In some embodiments, the charting module may include an equipment locating tag that may be in communication with the plurality of transceivers and the locating server of the high accuracy locating system may be operable to determine a location of the equipment locating tag in the healthcare facility within three feet or less of an actual location of the equipment locating tag. It is within the scope of the present disclosure that the plurality of transceivers may communicate via ultra-wideband (UWB) signals with the caregiver locating tag and the equipment locating tag. The locations of the caregiver locating tag and the equipment locating tag may be determined by the locating server using two way ranging and time difference of arrival (TDOA) techniques. Furthermore, the locating server may use signals from only a subset of the plurality of transceivers to determine the locations of the caregiver locating tag and the equipment locating tag. The subset may be determined based on signal strength of signals between the caregiver locating tag and the plurality of transceivers and between and the equipment locating tag and the plurality of transceivers, respectively. The subset for each of the caregiver locating tag and the equipment locating tag, respectively, may include at least three transceivers from the plurality of transceivers that may have highest signal strength values as compared to others of the plurality of transceivers.

The charting system contemplated herein further may include a remote computer that may be communicatively coupled to the voice-to-text module via the network. In such embodiments, the processor may be configured to initiate transmission of the at least one vital sign to the remote computer via the network after conversion of the at least one vital sign to text such that the at least one vital sign may be sent to at least two computers.

According to another aspect of the present disclosure, a charting system may include a vital sign monitor that may be configured to read at least one vital sign from a patient that may be located in a patient room. The charting system may also include a communication device that may have a processor and a microphone that may be coupled to the processor and that may be configured to receive voice inputs from a caregiver. The processor may operate a voice-to-text algorithm. The processor also may receive vital signs data from the vital signs monitor. The charting system may further have an electronic medical record (EMR) computer that may be communicatively coupled to the communication device. The charting system also may have a locating system that may include locating receivers situated throughout the healthcare facility and a caregiver locating tag that may be worn by the caregiver. The caregiver locating tag may communicate with one or more of the locating receivers that may be in communicative proximity with the caregiver locating tag. The locating system further may include a locating server that may be communicatively coupled to the locating receivers. The locating server may be configured to notify the processor that the caregiver may have entered the patient room. The voice-to-text algorithm may be activated in response to the caregiver entering the patient room and may be configured to receive dictation from the caregiver via the microphone after activation. The voice-to text algorithm may convert the dictation into text. The processor may initiate transmission of the text and the vital signs data from the vital sign monitor to the EMR computer.

In some embodiments, the communication device may include one or more of the following: a patient bed that may be located in a patient room, a caregiver locating tag that may be worn by the caregiver, an audio station of a nurse call system, or a computer located in the patient room. The vital sign monitor may be activated to read the at least one vital sign in response to the caregiver entering the patient's room. Optionally, the caregiver locating tag may include a plurality of buttons. Each button of the plurality of buttons may be related to a respective caregiver activity. Furthermore, each button of the plurality of buttons may be selectable by the caregiver to convey information about the respective caregiver activity to the EMR computer. If desired, a time that the caregiver selects each button of the plurality of buttons may be communicated to the EMR computer. The respective caregiver activity for at least one of the buttons of the plurality of buttons may include at least one of the following: completion of caregiver rounds, medication administration, or completion of physical therapy.

It is contemplated by this disclosure that the locating system may be operable to identify which caregiver may have entered the patient room and the EMR computer may be configured to record which caregiver may have entered the patient room in response to receipt of a message from the locating server. In some embodiments, the locating system may include a high accuracy locating system in which the locating server may be operable to determine a location of the caregiver locating tag in the healthcare facility within three feet or less of an actual location of the caregiver locating tag. The plurality of transceivers may communicate via ultra-wideband (UWB) signals with the caregiver locating tag. Optionally, the location of the caregiver locating tag may be determined by the locating server using two way ranging and time difference of arrival (TDOA) techniques.

In some embodiments, the locating server may use signals from only a subset of the plurality of transceivers to determine the location of the caregiver locating tag. For example, the subset may be determined based on signal strength of signals between the caregiver locating tag and the plurality of transceivers. The subset may include at least three transceivers from the plurality of transceivers that may have highest signal strength values as compared to others of the plurality of transceivers.

The charting system may further include a remote computer that may be communicatively coupled to the processor of the communication device. In such embodiments, the processor may be configured to initiate transmission of the text and the at least one vital sign to the remote computer after conversion of the dictation to text such that the dictation and at least one vital sign may be sent to at least two computers.

According to a further aspect of the present disclosure, a charting system for use in a healthcare facility having a network may include an electronic medical record (EMR) computer that may be located in a patient room of a patient, an EMR server that may be located remotely from the EMR computer and that may be communicatively coupled to the EMR computer via the network, a caregiver locating tag that may be worn by a caregiver, and a dongle that may be communicatively coupled to the EMR computer. The dongle may have a microphone, a speaker, a processor that may be coupled to the microphone and to the speaker, and wireless communication circuitry that may be coupled to the processor and configured to detect the caregiver locating tag when the caregiver may be in the patient room. The processor may have instructions that, when executed, may result in the following: (i) an audible prompt may be played through the speaker based on detection by the wireless communication circuitry of the caregiver locating tag in the patient room, and the audible prompt may remind the caregiver to populate an electronic medical record of the patient with patient vital signs information, (ii) receiving voice input from the caregiver via the microphone, (iii) converting the voice input from the caregiver into text, and (iv) transmitting the text to the EMR computer.

In some embodiments, the EMR computer may transmit the text received from the processor of the dongle to the EMR server via the network. The EMR server may store information in the electronic medical record of the patient based on the text received by the EMR computer. Optionally, the EMR server may parse sub-portions of the text for storage based on keywords in the text. For example, the keywords may identify types of vital signs of the patient that may be included in the text.

It is contemplated by this disclosure that the audible prompt may include a series of audible prompts that may request specific vital signs information be spoken by the caregiver for input into an electronic medical record of the patient such that one piece of vital signs information may be charted at a time before a subsequent audible prompt in the series may be played through the speaker. Thus, the processor may be configured to determine whether a keyword may be spoken by the caregiver to indicate that the specific vital signs information associated with the most recent audible prompt may not be available for charting. In such instances, the processor may be configured to play the subsequent audible prompt in the series of audible prompts in response to determining that the keyword was spoken by the caregiver. Optionally, the series of audible prompts may include prompts for the caregiver to verbally state two or more of the following vital signs of the patient: heart rate, respiration rate, blood pressure, oxygen saturation, or temperature.

In some embodiments, the instructions of the processor, when executed, further may result in one or more additional audible prompts being played through the speaker based on detection by the wireless communication circuitry of the caregiver locating tag in the patient room. For example, the one or more additional audible prompts may remind the caregiver to populate the electronic medical record of the patient with clinical inputs relating to one or more conditions of the patient that do not correspond to vital signs of the patient. The clinical inputs may include information regarding one or more of the following: patient complexion, pain level of the patient, bruising of the patient, or any rashes on the patient.

Optionally, the processor may implement a delay time after detection of the caregiver in the patient room before the audible prompt is played through the speaker. In such embodiments, the processor may play the audible prompt through the speaker after the delay time only if the wireless communication circuitry still detects that the caregiver locating tag is in the patient room.

According to yet another aspect of the present disclosure, a charting system for use in a healthcare facility having a network may include an electronic medical record (EMR) computer that may be located in a patient room of a patient and that may be communicatively coupled to the network. The system may have an EMR server that may be located remotely from the EMR computer and that may be communicatively coupled to the EMR computer via the network. The system may further have a locating system that may include locating receivers situated throughout the healthcare facility and a caregiver locating tag that may be worn by a caregiver. The caregiver locating tag may communicate with one or more of the locating receivers that may be in communicative proximity with the caregiver locating tag. The locating system further may include a locating server that may be communicatively coupled to the locating receivers. The locating server may be configured to notify the EMR computer via the network of the caregiver locating tag being located in the patient room. The system may have a dongle that may be communicatively coupled to the EMR computer. The dongle may include a microphone, a speaker, and a processor that may be coupled to the microphone and to the speaker. The processor may have instructions that, when executed, may result in the following: (i) an audible prompt being played through the speaker in response to notification from the locating system of the caregiver locating tag being located in the patient room, the audible prompt reminding the caregiver to populate an electronic medical record of the patient with patient vital signs information, (ii) receiving voice input from the caregiver via the microphone, (iii) converting the voice input from the caregiver into text, and (iv) transmitting the text to the EMR computer.

In some embodiments, the EMR computer may transmit the text received from the processor of the dongle to the EMR server via the network. In turn, the EMR server may store information in the electronic medical record of the patient based on the text received by the EMR computer. The EMR server may parse sub-portions of the text for storage based on keywords in the text. For example, the keywords may identify types of vital signs of the patient that may be included in the text.

It is contemplated by this disclosure that the audible prompt may include a series of audible prompts that may request specific vital signs information be spoken by the caregiver for input into an electronic medical record of the patient such that one piece of vital signs information may be charted at a time before a subsequent audible prompt in the series may be played through the speaker. If desired, the processor may be configured to determine whether a keyword may be spoken by the caregiver to indicate that the specific vital signs information associated with the most recent audible prompt may not be available for charting. In such embodiments, the processor may be configured to play the subsequent audible prompt in the series of audible prompts in response to determining that the keyword was spoken by the caregiver. The series of audible prompts may include prompts for the caregiver to verbally state two or more of the following vital signs of the patient: heart rate, respiration rate, blood pressure, oxygen saturation, or temperature.

In some embodiments, the instructions of the processor, when executed, further may result in one or more additional audible prompts being played through the speaker in response to notification from the locating system of the caregiver locating tag being located in the patient room. The one or more additional audible prompts may remind the caregiver to populate the electronic medical record of the patient with clinical inputs relating to one or more conditions of the patient that do not correspond to vital signs of the patient. For example, the clinical inputs may include information regarding one or more of the following: patient complexion, pain level of the patient, bruising of the patient, or any rashes on the patient.

In some embodiments, the locating system may include a high accuracy locating system in which the locating server may be operable to determine a location of the caregiver locating tag in the healthcare facility within three feet or less of an actual location of the caregiver locating tag. In such embodiments, the plurality of receivers may include a plurality of transceivers. The audible prompt may be played through the speaker in response to notification from the locating system that the caregiver locating tag may be located within three feet or less of the EMR computer or the dongle. For example, the plurality of transceivers communicates via ultra-wideband (UWB) signals with the caregiver locating tag. Thus, the location of the caregiver locating tag may be determined by the locating server using two way ranging and time difference of arrival (TDOA) techniques if desired.

It is contemplated by the present disclosure that the locating server may use signals from only a subset of the plurality of transceivers to determine the location of the caregiver locating tag. For example, the subset may be determined based on signal strength of signals between the caregiver locating tag and the plurality of transceivers. The subset may include at least three transceivers from the plurality of transceivers having highest signal strength values as compared to others of the plurality of transceivers.

According to still a further aspect of the present disclosure, a charting system for a healthcare facility may include a patient bed to support a patient in a patient room, a vital sign monitor configured to read at least one vital sign from the patient, an electronic medical record (EMR) computer that may be communicatively coupled to the vital sign monitor, and a high accuracy locating system that may be communicatively coupled to the vital sign monitor. The high accuracy locating system may include locating transceivers that may be situated throughout the healthcare facility and a caregiver locating tag that may be worn by a caregiver. The caregiver locating tag may communicate with one or more of the locating transceivers that may be in communicative proximity with the caregiver locating tag. The locating system further may include a locating server that may be communicatively coupled to the locating transceivers and operable to determine a location of the caregiver locating tag in the healthcare facility within three feet or less of an actual location of the caregiver locating tag. The locating server may be configured to send a first message to the vital sign monitor to start reading the at least one vital sign from the patient in response to detection that the caregiver locating tag may have entered the patient room. The locating server may be configured to send a second message to the vital sign monitor to transmit vital sign information as read by the vital sign monitor to the EMR computer in response to detection that the caregiver locating tag may be within a threshold distance of the patient bed.

In some embodiments, the plurality of transceivers may communicate via ultra-wideband (UWB) signals with the caregiver locating tag. Optionally, the location of the caregiver locating tag may be determined by the locating server using two way ranging and time difference of arrival (TDOA) techniques. The locating server may use signals from only a subset of the plurality of transceivers to determine the location of the caregiver locating tag. For example, the subset may be determined based on signal strength of signals between the caregiver locating tag and the plurality of transceivers. The subset may include at least three transceivers from the plurality of transceivers having highest signal strength values as compared to others of the plurality of transceivers.

Optionally, the high accuracy locating system may include an equipment locating tag that may be attached to the patient bed and that may be in communication with the plurality of transceivers. The locating server of the high accuracy locating system may be operable to determine a location of the equipment locating tag in the healthcare facility within three feet or less of an actual location of the equipment locating tag. The threshold distance between the caregiver locating tag and the patient bed may be determined based on a tag distance between the caregiver locating tag and the equipment locating tag.

According to yet a further aspect of the present disclosure, a caregiver locating tag for use with a real time locating system (RTLS) in a healthcare facility having a network may be provided. The caregiver locating tag may include a housing, a microphone that may be carried by the housing and that may be configured to receive voice inputs from a caregiver, and at least one processor that may be carried by the housing. The at least one processor may be communicatively coupled to the microphone and the at least one processor may operate a voice-to-text algorithm. The caregiver locating tag also may include wireless communication circuitry that may be carried by the housing and that may be configured to communicate with the RTLS and with the network. The caregiver locating tag may further include a plurality of buttons that may be carried by the housing and that may be communicatively coupled to the at least one processor. A first button of the plurality of buttons when selected may enable the voice-to-text algorithm so that words spoken by the caregiver may be input to the processor via the microphone and may be converted to text in accordance with the voice-to-text algorithm. The voice-to-text algorithm may be disabled prior to selection of the first button. A second button of the plurality of buttons when selected may indicate completion of a caregiver activity.

In some embodiments, the caregiver activity associated with the second button of the plurality of buttons may include at least one of the following: completion of caregiver rounds, medication administration, completion of physical therapy, or taking of the at least one vital sign. Optionally, the processor may signal the wireless communication circuitry to transmit the text to the network. Alternatively or additionally, the processor may signal the wireless communication circuitry to transmit to the network information corresponding to the completion of the caregiver activity indicated by the selection of the second button.

The wireless communication circuitry may include a first antenna to transmit the text to the network according to a first communication technology and a second antenna to transmit a tag identification (ID) according to a second communication technology. For example, the first communication technology may include WiFi technology and the second communication technology may include ultra-wideband (UWB) technology, just to name a couple. If desired, the first antenna also may be used to transmit the tag ID along with the text according to the first communication technology. In some embodiments, the at least one processor may include a first processor that may run the voice-to-text algorithm in response to selection of the first button and a second processor that may control transmission of a tag identification (ID) via the wireless communication circuitry. The second button may be communicatively coupled to the first processor.

According to yet still another aspect of the present disclosure, a caregiver locating tag for use with a real time locating system (RTLS) and an electronic medical records (EMR) system in a healthcare facility having a network and a plurality of patient rooms may be provided. The caregiver locating tag may include a housing, at least one processor that may be carried by the housing, and wireless communication circuitry that may be carried by the housing and that may be configured to communicate with the RTLS and with the network. The wireless communication circuitry may be communicatively coupled to the processor. The processor may control the wireless communication circuitry to transmit a tag identification (ID) that is received by the RTLS and that is used by the RTLS in connection with determining a location of the caregiver locating tag in the healthcare facility. The caregiver locating tag also may have a plurality of buttons that may be carried by the housing and that may be communicatively coupled to the at least one processor. Each button of the plurality of buttons may correspond to a respective caregiver activity. Selection of each button may indicate completion of the respective caregiver activity. In response to selection of each button, the processor may command the wireless communication system to transmit information regarding completion of the respective caregiver activity to the EMR system for charting in an electronic medical record of a patient associated with a patient room of the plurality of patient rooms in which the caregiver is located at the time of pressing the respective button.

In some embodiments, the plurality of buttons may include a first button and a second button. The caregiver activity associated with the first button may include one of the following: completion of caregiver rounds, medication administration, completion of physical therapy, or taking of the at least one vital sign, and the caregiver activity associated with the second button may include another one of the following: completion of caregiver rounds, medication administration, completion of physical therapy, or taking of the at least one vital sign. Optionally, the plurality of buttons may include a third button and the caregiver activity associated with the third button may include yet another one of the following: completion of caregiver rounds, medication administration, completion of physical therapy, or taking of the at least one vital sign. Further optionally, the plurality of buttons may include a fourth button and the caregiver activity associated with the fourth button may include a remaining one of the following: completion of caregiver rounds, medication administration, completion of physical therapy, or taking of the at least one vital sign.

In some embodiments, the wireless communication circuitry may include a first antenna to transmit the information regarding completion of the respective caregiver activity to the EMR system via the network according to a first communication technology and a second antenna to transmit the tag ID according to a second communication technology. For example, the first communication technology may include WiFi technology and the second communication technology may include ultra-wideband (UWB) technology. If desired, the first antenna also may be used to transmit the tag ID along with the information regarding completion of the respective caregiver activity according to the first communication technology.

It is contemplated by the present disclosure that the at least one processor may include a first processor and a second processor. The first processor may be coupled to the plurality of buttons and to the wireless communication circuitry, and the second processor may be configured to control transmission of the tag ID via the wireless communication circuitry.

The caregiver locating tag further may include a microphone that may be carried by the housing and a start/stop button. The microphone and the start/stop button may be coupled to the processor. The processor may be configured to execute a voice-to-text algorithm to convert speech received by the microphone into text for transmission to the EMR system via the wireless communication circuitry and the network. The start/stop button may be used to enable and disable the voice-to-text algorithm. For example, the voice-to-text algorithm may be enabled in response to the start/stop button being pressed a first time and the voice-to-text algorithm may be disabled in response to the start/stop button being pressed a second time such that successive presses of the start/stop button may enable and disable the voice-to-text algorithm in succession. Alternatively or additionally, the voice-to-text algorithm may be enabled in response to the start/stop button being pressed and held and wherein the voice-to-text algorithm may be disabled in response to the start/stop button being released.

In some embodiments, the caregiver locating tag further may include at least one vitals charting button that may be carried by the housing and that may be communicatively coupled to the processor. Selection of the at least one vitals charting button may result in patient vital signs data from at least one piece of vital sign monitoring equipment being charted in the electronic medical record of the patient associated with the patient room of the plurality of patient rooms in which the caregiver is located at the time of selection of the at least one vitals charting button. The at least one vitals charting button may include a first button that, when selected, may result in patient vital signs data from multiple pieces of vital sign monitoring equipment being charted in the electronic medical record of the patient. For example, the multiple pieces of vital monitoring equipment may include at least two of the following: a heart rate monitor, a respiration rate monitor, a blood pressure monitor, a temperature monitor, or a pulse oximeter.

According to some embodiments of the caregiver locating tag, the at least one vitals charting button may include a first button and a second button. The at least one piece of vital sign monitoring equipment may include a first vital sign monitor and a second vital sign monitor. Selection of the first button may result in a first vital sign acquired from the patient by the first vital sign monitor being charted in the electronic medical record of the patient, and selection of the second button may result in a second vital sign acquired from the patient by the second vital sign monitor being charted in the electronic medical record of the patient.

The first vital sign monitor may include a first one of the following: a heart rate monitor, a respiration rate monitor, a blood pressure monitor, a temperature monitor, or a pulse oximeter; and the second vital sign monitor may include a second one of the following: a heart rate monitor, a respiration rate monitor, a blood pressure monitor, a temperature monitor, or a pulse oximeter. The at least one vitals charting button may include a third button, the at least one piece of vital sign monitoring equipment may include a third vital sign monitor, and the third vital sign monitor may include a third one of the following: a heart rate monitor, a respiration rate monitor, a blood pressure monitor, a temperature monitor, or a pulse oximeter.

If desired, the at least one vitals charting button may include a fourth button, the at least one piece of vital sign monitoring equipment may include a fourth vital sign monitor, and the fourth vital sign monitor may include a fourth one of the following: a heart rate monitor, a respiration rate monitor, a blood pressure monitor, a temperature monitor, or a pulse oximeter. The at least one vitals charting button may include a fifth button, the at least one piece of vital sign monitoring equipment may include a fifth vital sign monitor, and the fifth vital sign monitor may include a remaining one of the following: a heart rate monitor, a respiration rate monitor, a blood pressure monitor, a temperature monitor, or a pulse oximeter.

According to yet still a further aspect of the present disclosure, a caregiver locating tag for use with a real time locating system (RTLS) and an electronic medical records (EMR) system in a healthcare facility having a network and a plurality of patient rooms may be provided. The caregiver locating tag may include a housing, at least one processor that may be carried by the housing, and wireless communication circuitry that may be carried by the housing and that may be configured to communicate with the RTLS and with the network. The wireless communication circuitry may be communicatively coupled to the processor. The processor may control the wireless communication circuitry to transmit a tag identification (ID) that is received by the RTLS and that is used by the RTLS in connection with determining a location of the caregiver locating tag in the healthcare facility. The caregiver locating tag also may include at least one vitals charting button that may be carried by the housing and that may be communicatively coupled to the processor. Selection of the at least one vitals charting button may result in patient vital signs data from at least one piece of vital sign monitoring equipment being transmitted to the EMR system via the network and charted in the electronic medical record of the patient associated with the patient room of the plurality of patient rooms in which the caregiver is located at the time of selection of the at least one vitals charting button.

In some embodiments, the at least one vitals charting button may include a first button that, when selected, results in patient vital signs data from multiple pieces of vital sign monitoring equipment being charted in the electronic medical record of the patient. For example, the multiple pieces of vital sign monitoring equipment may include at least two of the following: a heart rate monitor, a respiration rate monitor, a blood pressure monitor, a temperature monitor, or a pulse oximeter. Alternatively or additionally, the at least one vitals charting button may include a first button and a second button. The at least one piece of vital sign monitoring equipment may include a first vital sign monitor and a second vital sign monitor. Selection of the first button may result in a first vital sign acquired from the patient by the first vital sign monitor being charted in the electronic medical record of the patient, and selection of the second button may result in a second vital sign acquired from the patient by the second vital sign monitor being charted in the electronic medical record of the patient.

The first vital sign monitor may include a first one of the following: a heart rate monitor, a respiration rate monitor, a blood pressure monitor, a temperature monitor, or a pulse oximeter; and the second vital sign monitor may include a second one of the following: a heart rate monitor, a respiration rate monitor, a blood pressure monitor, a temperature monitor, or a pulse oximeter. Optionally, the at least one vitals charting button may include a third button, the at least one piece of vital sign monitoring equipment may include a third vital sign monitor, and the third vital sign monitor may include a third one of the following: a heart rate monitor, a respiration rate monitor, a blood pressure monitor, a temperature monitor, or a pulse oximeter.

If desired, the at least one vitals charting button may include a fourth button, the at least one piece of vital sign monitoring equipment may include a fourth vital sign monitor, and the fourth vital sign monitor may include a fourth one of the following: a heart rate monitor, a respiration rate monitor, a blood pressure monitor, a temperature monitor, or a pulse oximeter. The at least one vitals charting button may include a fifth button, the at least one piece of vital sign monitoring equipment may include a fifth vital sign monitor, and the fifth vital sign monitor may include a remaining one of the following: a heart rate monitor, a respiration rate monitor, a blood pressure monitor, a temperature monitor, or a pulse oximeter.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
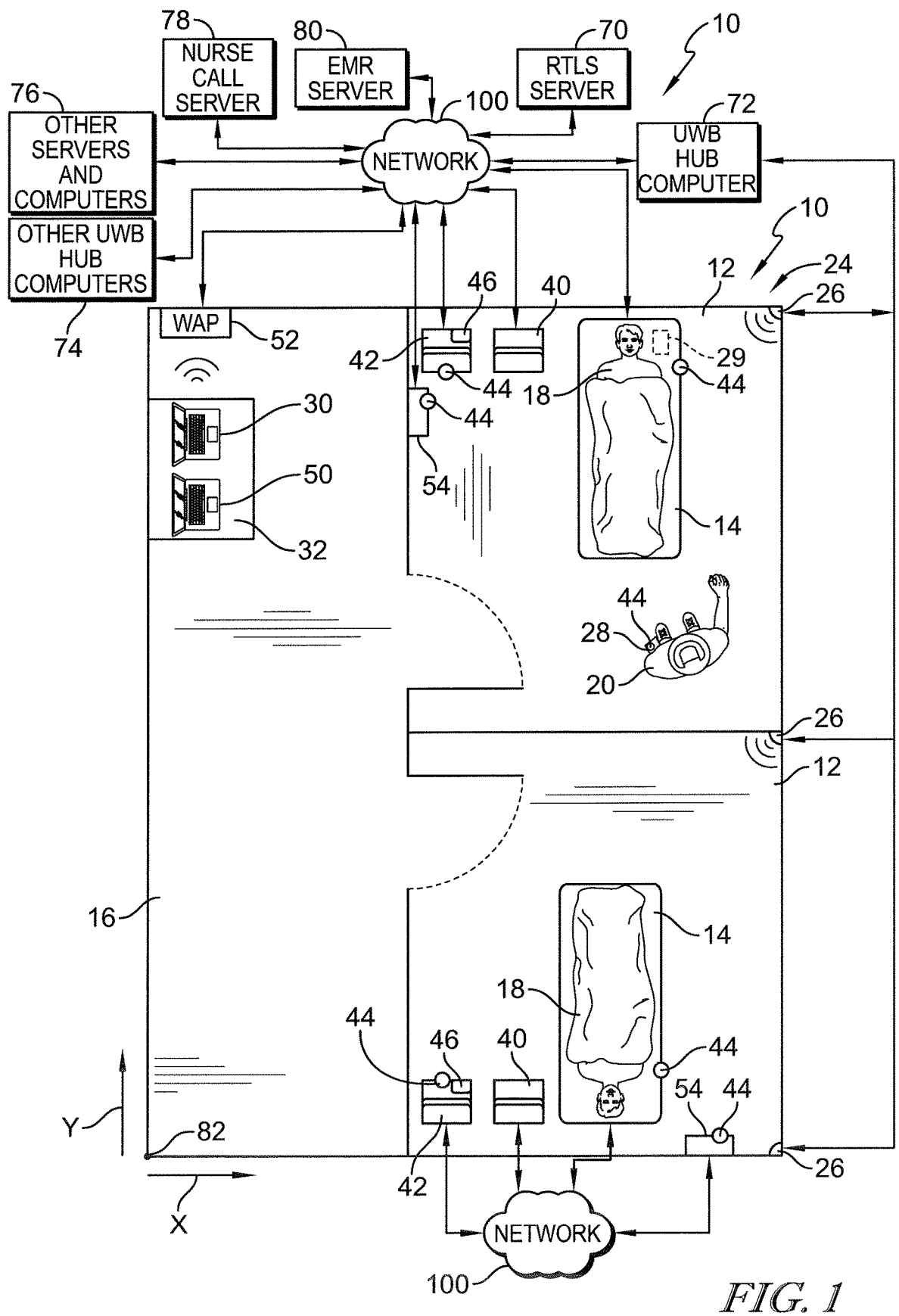
FIG. 1 is a diagrammatic view showing a portion of a healthcare facility having two patient rooms with patient beds supporting respective patients, a vital sign monitor in each room, an electronic medical record (EMR) computer in each room, an EMR server coupled to the vital sign monitors and EMR computers via a network, a real time locating system (RTLS) including a caregiver location tag worn by a caregiver in one of the rooms and including transceivers in communication with an ultra-wide band (UWB) hub computer, the RTLS tracking the location of the caregiver locating tag in the healthcare facility, and showing an audio station of a nurse call system mounted to a wall of the patient room and coupled to a nurse call server via the network, each of the patient beds, the EMR computers, the audio stations, and the caregiver locating tag having a microphone (indicated by a circle) into which the caregiver speaks to chart vital signs information and other clinical inputs into an electronic medical record of the respective patient.

Referring to FIG. 1, a health care information system 10 is provided in a healthcare facility having a plurality of patient rooms 12. In the illustrative example, two patient rooms 12 are shown for the sake of discussion; however, it will be appreciated that typical healthcare facilities have more than two patient rooms 12. The patient rooms 12 each include a patient support apparatus 14. The patient support apparatus 14 is illustrated as a patient bed; however, other patient support apparatuses such as a bench, a stretcher, a wheel chair, and the like, are contemplated by this disclosure and are sometimes also present in patient rooms 12. Each of the illustrative patient beds 14 supports a patient 18 thereon. A caregiver 20 is located in one of the patient rooms 12 to assess the respective patient 18.

This disclosure pertains primarily to systems and methods that permit caregivers 20 to chart vital signs data (aka vitals) to an electronic medical record (EMR) of the patient in an EMR system. In connection with charting the vital signs data to the EMR, the caregiver is able to provide comments or other clinical inputs or observations relating to the charted data or related to the respective patient 18. The caregiver 20 may also enter the patient room 12 of a respective patient 18 to dispense medication to the patient 18 or otherwise check on the patient 18 according to a rounding regimen and, optionally, these events are also charted to the patient's EMR according to this disclosure.

The overall system 10 is subdivided into sub-systems which are themselves, also referred to herein as "systems." For example, system 10 includes a real time locating system (RTLS) 24 that tracks the locations of caregivers and equipment throughout the facility. In some embodiments, RTLS 24 is embodied as a high-accuracy locating system such as an ultra-wideband (UWB) locating system, but this need not be the case in other embodiments. RTLS 24 includes a plurality of transceivers 26 positioned throughout the healthcare facility such as in the patient rooms 12, in the hallway 16 of the healthcare facility 10, and in other locations throughout the healthcare facility (e.g., staff break rooms, bathrooms, pharmacy, treatment rooms, imaging rooms, laboratories, cafeteria, etc.) at the discretion of the system designer.

The transceivers 26 receive wireless transmissions from caregiver location tags 28 that are worn by respective caregivers 20 and by equipment tags 29 that are attached to various pieces of equipment such as patient beds 14. In the example of FIG. 1, one tag 28 is coupled to the clothing of the caregiver 20, such as with a clip, and another tag 29 (in phantom) is attached to the patient bed 14. Tags 28 may instead be worn around the caregiver's neck on a necklace or attached to the caregiver's wrist on a wristband or bracelet, for example.

In some embodiments, the tags 28, 29 receive a signal from the transmitter circuitry of one or more of the transceivers 26 and, in response, transmit a return signal to at least one of the transceivers 26. The return signal includes a tag identification (ID) which is unique to each tag 28, 29. Such an arrangement preserves battery life of tags 28, 29 because transmissions of tag ID's are only made by the tags 28, 29 when in communicative proximity of one or more transceivers 26 and after receiving a request signal from at least one of the transceivers. In other embodiments, tags 28, 29 transmit their respective tag ID's on a periodic basis. In still other embodiments, short range wireless beacons or infrared transmitters are mounted at fixed locations throughout the healthcare facility and send a signal with a location ID to the tags 28, 29 that are in the vicinity of the short range beacons and, in response to receipt of the signal, the tags 28, 29 transmit their respective tag ID's and location ID's to transceivers 26. In each of these embodiments, transceivers 26 transmit the received tag ID or tag ID's to an RTLS server 70 along with a respective transceiver ID and, if applicable, the location ID.

In some embodiments, the transceiver ID's correlate to particular locations in the healthcare facility. Thus, the RTLS server 70 determines the locations of tags 28, 29 within the healthcare facility by correlating the tag ID's with the receiver ID's (and/or the location ID's, if applicable) and, ultimately, with the location correlated with the receiver ID's and/or location ID's. RTLS server 70 also correlates the tag ID's with the respective caregivers wearing tags 28 and with the equipment to which tags 29 are attached. In some embodiments, patients 18 also have tags for tracking the whereabouts of the patients 18 throughout the healthcare facility. Thus, in some embodiments, the RTLS system 24 of overall system 10 includes tags 28, 29, transceivers 26, and RTLS server 70. Tags 28, 29 are sometimes referred to as "badges" and so the terms "tag" and "badge" are used interchangeably herein.

System 10 includes network infrastructure which is designated diagrammatically as network 100 in FIG. 1. Network 100 is intended to represent the infrastructure (e.g., wireless access points, Ethernet jacks such as RJ-45 connectors, wires, routers, gateways, etc.) provided in a healthcare facility and the various computer devices (e.g., personal computers, servers, laptop computers, patient care equipment, etc.) that are coupled to the infrastructure. The various subsystems described herein include components that may communicate with each other using portions of network 100. In the illustrative example, transceivers 26 communicate with RTLS server 70 via portions of network 100.

In some embodiments, tags 28, 29 communicate wirelessly with receivers 26 using infrared (IR) technology. In such embodiments, line of sight between tags 28, 29 and one or more of receivers 26 needs to remain unobstructed in order for communication to be established between the tags 28, 29 and one or more of the transceivers 26 to determine the location of the tags 28, 29 in the healthcare facility. Thus, the IR signals cannot pass through walls, equipment, and people located in the room. In general, RTLS systems 24 that use IR communication between tags 28, 29 and transceivers 26 are able to reliably determine that the tags 28, 29 are located inside a particular room, but are not able to determine the exact location, within a relatively small accuracy threshold, of the tag 28, 29 within the room.

As noted above, RTLS 24 in some embodiments is embodied as a high-accuracy locating system such as an ultra-wideband (UWB) locating system. In such embodiments, tags 28, 29 are configured as UWB tags 28, 29 having UWB transceivers, and transceivers 26 are configured as UWB transceivers. The UWB transceivers 26 are stationary and the UWB transceivers of tags 28, 29 are mobile, but their circuitry otherwise may be substantially the same. Thus, tags 28, 29 and transceivers 26 each include a housing that contains associated circuitry. The circuitry of tags 28, 29 and transceivers 26 includes for example a processor such as a microprocessor or microcontroller or the like, memory for storing software, and communications circuitry including a transmitter, a receiver and at least one antenna, for example. Transceivers 26 each include mounting hardware, such as brackets or plates or the like, in some embodiments, to permit the transceivers 26 to be mounted at fixed locations in the rooms 12 and other locations of the healthcare facility with fasteners such as screws or the like.

In the illustrative example of system 10 of FIG. 1, the RTLS 24 further includes an UWB hub computer 72 which is communicatively coupled to other UWB hub computers 74 of RTLS 24 via network 100 of the healthcare facility. In the illustrative example, RTLS 24 is also communicatively coupled to other servers and computers 76 of the healthcare facility and to a nurse call server 78 and an EMR server 80. The other servers and computers 76 generically represents all other computers and servers of network 100 in a healthcare facility such as, for example, an admission/discharge/transfer (ADT) computer.

As shown in FIG. 1, various lines with double headed arrows interconnect transceivers 26 with hub computer 72 and interconnect servers and computers 70, 72, 74, 76, 78, 80 with each other via network 100. It should be appreciated that these lines with double headed arrows represent bidirectional communication over wired data links (including electrical wires or fiber optic data links) and/or wireless data links, at the discretion of the designer of system 10. UWB transceivers 26 communicate wirelessly with tags 28, 29 using radio frequency (RF). It is known that RF signals are able to pass through walls, ceilings, floors, and other objects such as people and equipment. Thus, according to this disclosure, it is not required that each room 12 has a transceiver 26 located therein in embodiments of RTLS 24 using RF communication.

According to this disclosure, the RTLS 24 that operates as a high-accuracy locating system using UWB technology is able to determine the location of each tag 28, 29 that is in communication with at least three of transceivers 26 within about one foot (30.48 cm) or less of the tag's actual location. In other embodiments, RTLS 24 is able to determine the location of each tag 28, 29 that is in communication with at least three of transceivers 26 within about three feet (91.44 cm) or less of the tag's actual location and such embodiments are still considered to be high-accuracy locating systems according to the present disclosure.

In some embodiments, the high-accuracy RTLS 24 is operable to determine the location of tags 28, 29 in 3-dimensional space. However, in many embodiments, it suffices to determine the location of tags 28, 29 in 2-dimensional space. Accordingly, FIG. 1 shows X and Y directions relative to a floor plan of the healthcare facility with point 82 serving as an arbitrary origin of an X-Y coordinate system. The Z dimension corresponds to a height in a Z direction (not shown) above the floor plan of FIG. 1. UWB locating systems typically operate within the 3.1 gigahertz (GHz) to 10.6 GHz frequency range. Suitable transceivers 26 in this regard include WISER Mesh Antenna Nodes and suitable tags 28, 29 in this regard include Mini tracker tags, all of which are available from Wiser Systems, Inc. of Raleigh, North Carolina and marketed as the WISER LOCATOR™ system.

In some embodiments, the high-accuracy RTLS system 24 implementing UWB technology uses 2-way ranging, clock synchronization, and time difference of arrival (TDoA) techniques to determine the locations of tags 28, 29 in the X and Y directions (and, optionally, the Z direction in some embodiments). See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system. Using these techniques, distances between the stationary transceivers 26 and the various mobile tags 28, 29 are determined based on bidirectional wireless signals communicated between tags 28, 29 and transceivers 26. For example, the distance from each transceiver 26 to any particular tag 28, 29 can be resolved onto the X-Y plane as a circle having a radius equal to the distance and having its center at the particular transceiver 26. The actual location of the mobile tag 28, 29 is determined based on the point of intersection of three or more of the circles defined by radii from three or more corresponding transceivers 26.

It should be appreciated that, unless a tag 28, 29 is midway between two transceivers 26 on a straight line connecting the two transceivers 26 (in which case the two circles generated will be tangent to each other at a single point), then two circles that are generated from the two transceivers 26 will intersect at two points such that a circle generated from a third transceiver 26 is needed to determine which of the two points is the one corresponding to the location of the tag 28, 29. Generating fourth, fifth, sixth, etc. circles having other transceivers 26 as their respective centers will further increase the accuracy of determining the actual location of the particular tag 28, 29. Due to small errors introduced by refraction of the RF signal through solid objects, including walls, people, equipment, etc., the three or more circles in many instances will not intersect at exactly the same point and so interpolation between clusters of circle intersections is performed to arrive at the calculated location of the particular mobile tag 28, 29 of interest on the X-Y plane. These considerations are discussed in International Publication No. WO 2017/083353 A1 which is already incorporated by reference herein.

Tracking the locations of multiple mobile tags 28, 29 in substantially real time using 2-way ranging, clock synchronization, TDoA, resolution of circles onto the X-Y plane, and interpolating intersection point clusters of the circles requires a large amount of computational power by hub computers 72, 74 and/or the associated RTLS server 70. Thus, each hub computer 72, 74 receives incoming data from a predetermined number of transceivers 26. In the illustrative example of FIG. 1, hub computer 72 receives data from three transceivers 26. TDC Acquisition Holdings, Inc. of Huntsville, Alabama which does business as Time Domain, makes a hub computer (referred to as the PLUS Synchronization Distribution Panel) that is capable of receiving incoming data from up to 144 transceivers. The locating server or computer 72, in turn, receives data from the various hubs 72, 74 and tracks or monitors the locations of tags 28, 29 in the healthcare facility.

Regardless of the number of transceivers 26 coupled to hub computers 72, 74, it is contemplated by the present disclosure that, in some embodiments, locating server 70 and/or hub computers 72, 74 are programmed to use signals from only a subset of the plurality of transceivers 26 to determine the location of any given caregiver locating tag 28. For example, the subset may be determined based on signal strength of signals between the caregiver locating tag 28 and the plurality of transceivers 26. The subset may include at least three transceivers 26 from the plurality of transceivers 26 having highest signal strength values as compared to others of the plurality of transceivers 26.

Regardless of the type of RTLS system used, the present disclosure contemplates that a position of the caregiver badges 28 and equipment badges 29 is able to be determined. That is, the RTLS 24 determines whether the caregiver 20 is in a particular patient room 12, the hallway 16, etc. The RTLS server 70 transmits signals indicative of the location of the tags 28, 29 to one or more other servers 78, 80, 76 in some embodiments. For example, a position of the caregiver 20 is monitored using a master nurse station computer 30 located at master nurse station 32 and/or is monitored using any other server or computer 76 in communication with RTLS server 70. In the illustrative FIG. 1 example, the master nurse station 32 is located in the hallway 16 outside of rooms 12. An EMR computer 50 is also located at master nurse station 32 in the illustrative example. Computers 30, 50 communicate wirelessly with a wireless access point (WAP) 52 which, in turn, is in communication with network 100. Thus, computers 30, 50 are in communication with servers 78, 80 via WAP 52 and network 100. Although one WAP 52 is shown in FIG. 1, it is contemplated by this disclosure that system 10 includes a multitude of WAP's 52 located throughout the healthcare facility and in communication with network 100.

Still referring to FIG. 1, a vital signs monitor 40 is positioned near and/or is coupled to the patient support apparatus 14. The vital signs monitor 40 monitors one or more vital signs of the patient 18, e.g. heartrate, blood pressure, respiratory rate, pulse oximetry, temperature, or the like, typically, via sensors that are attached to the patient 18. Although one vital signs monitor 40 is shown in FIG. 1, it should be understood that multiple vital signs monitors 40 may be present for monitoring different patient vital signs. The vital signs monitor 40 is electronically coupled to a room computer 42. In the illustrative example, the electronic coupling between monitor 40 and computer 42 occurs via network but in other embodiments, the electronic coupling occurs in-room between monitor 40 and computer 42 such as via a direct wired connection or via short-range wireless communication (e.g., Bluetooth communication or Bluetooth Low Energy (BLE) communications).

The room computer 42 receives vital signs data from monitor 40 and/or also receives other clinical inputs related to the patient 18 that are input by the caregiver 20. The other clinical inputs include, for example, subjective observations of the patient 18 made by the caregiver 20 such as, for example, information relating to the patient's skin condition, e.g. rashes, bruises, presence of any pressure ulcers, and complexion, and other information, such as general disposition of the patient, e.g. drowsiness, lightheadedness, etc. It is contemplated by this disclosure that, in some embodiments, the subjective clinical observations are input into computer 42 vocally by the caregiver 20 using a microphone 44 of computer 42. Computer 42 includes a voice-to-text module 46 which includes a voice-to-text algorithm or software that operates to convert the vocal input from microphone 44 into text for communication to EMR server 80 via network 100 for storing in the EMR of the patient 18 located in the same room 12 in which computer 42 is located. Examples of suitable voice-to-text software that may be stored in module 46 include the Watson Speech to Text software available from International Business Machines Corporation (IBM) of Armonk, New York and the NUANCE® DRAGON® software available from American Dictation Corp. of Wrentham, Massachusetts.

In some instances, one or more of the vital signs monitors 40 located in the room 12 with the patient 18 are standalone monitors 40 that are not coupled to any other computers or servers via network 100. It is contemplated by this disclosure that vitals from such standalone monitors 40 are also entered into the patient's EMR vocally using microphone 44 and voice-to-text module 46. Thus, voice-to-text module 46 is configured in some embodiments to detect that certain keywords are spoken to indicate that certain vitals (e.g., heartrate, respiration rate, pulse oximetry data, temperature, etc.) are being communicated vocally to module 46 of computer 42 or that the other clinical inputs are being communicated vocally to module 46 of computer 42.

In other embodiments, the microphone 44 and/or the voice-to-text module 46 is provided in other devices in room 12 as will be discussed in further detail below in connection with FIGS. 2-7. For example, in addition to, or in lieu of, microphone 44 being included as part of computer 42, one or more other microphones 44 may be included as part of the circuitry of the patient support apparatus 14, the caregiver badge 28, and/or an audio station 54 of a nurse call system of system 10. While it is contemplated that the voice-to-text module 46 will typically be included in the same device as microphone 44, this need not be the case. For example, in FIG. 1, each of the microphones 44 of bed 14, badge 28, and audio station 54 communicate voice signals to the voice-to-text module 46 of computer 42 which, in turn, converts the voice signals to text for delivery to the EMR of the patient 18 stored in server 80. Also in the FIG. 1 example, the voice signals are routed via the network 100 from each of bed 14, badge 28 and audio station 54 to module 46 of computer 42.

The caregiver 20 speaks the clinical inputs and/or vitals data into one of the microphones 44 which, in turn, sends the vocal clinical inputs and/or vitals data for receipt by module 46. The clinical input module 46 runs or executes the voice-to-text algorithm to convert the caregiver 20 dictation into text data that, in some embodiments, is saved within the voice-to-text module 46. In some embodiments, module 46 transmits the text data to EMR computer 50 at the nurse's station 32 in addition to, or in lieu of, providing the text data to the EMR server 80 for storage in the patient's EMR. The EMR computer 50 is used by the caregiver 20 to view the text data locally to confirm that the vitals data and clinical inputs information has been entered into the patient's EMR properly and if not, to make manual corrections to the patient's EMR with computer 50.

According to some embodiments of the present disclosure, RTLS 24 tracks the location of the caregiver 20 and in response to the caregiver 20 entering one of the patient rooms 12 or in response to the caregiver 20 being within a threshold distance (e.g., about three feet or less) of one of the devices 14, 28, 42, 54 having a microphone 44, the RTLS 24 notifies the computer 42 to activate or enable (e.g., turn on) the voice-to-text module 46 to begin recording or otherwise processing the caregiver dictation received at the microphone 44 of one of devices 14, 28, 42, 54. Alternatively or additionally, the caregiver 20 activates or enables the voice-to-text module 46 to begin receiving the caregiver dictation by engaging a user input, such as a button or icon on a graphical user interface (GUI), provided on one or more of devices 14, 28, 42, 54. In other embodiments, the voice-to-text algorithm of module 46 continuously monitors the microphones 44 for keywords included in the caregiver dictation. In response to the voice-to-text algorithm detecting a keyword from the caregiver 20, the voice-to-text module 46 begins recording or otherwise processing the caregiver dictation. Once activated, voice-to-text module 46 converts the caregiver dictation to text and transmits the text of the caregiver dictation, e.g. subjective clinical inputs, and the vital signs data from the vital signs monitor(s) 40 to the patient's EMR stored in server 80 and, in some embodiments, to EMR computer 50.

Figure 2:
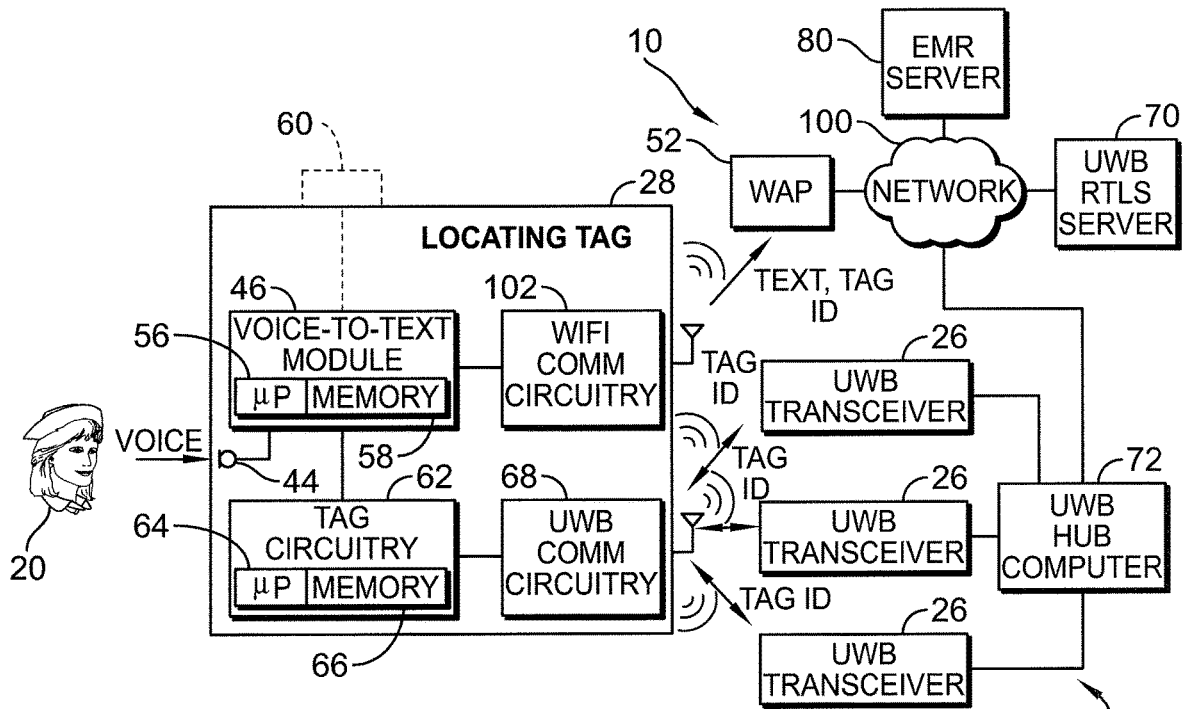
FIG. 2 is a block diagram of a first embodiment of a charting system showing the caregiver locating tag having a voice-to-text module, an optional user input (in phantom) to enable the voice-to-text module, a microphone coupled to the voice-to-text module to receive a voice input from the caregiver, WiFi communication circuitry that is coupled to the voice-to-text module operating to send text converted from the voice input from the caregiver by the voice-to-text module along with a tag identification (ID) to a wireless access point of the network for delivery to the EMR server for charting into a patient's electronic medical record, and showing the caregiver locating tag having tag circuitry coupled to the voice to text module and coupled to UWB communication circuitry that communicates wirelessly with three UWB transceivers that, in turn, are coupled to the UWB hub computer.

Referring now to FIG. 2, an embodiment is shown diagrammatically in which voice-to-text module 46 is included in caregiver locating tag 28. In the FIG. 2 embodiment, module 46 includes a microprocessor 56 and memory 58. The voice-to-text software is stored in memory 58 and is executed by microprocessor 56 in response to module 46 of tag 28 being activated, either in response to tag 28 being within a threshold distance to another piece of equipment such as bed 14 or vital signs monitor 40, or in response to the caregiver 20 pressing a button 60 (in phantom) included on tag 28 in some embodiments and electrically coupled to module 46. Module 46 of tag 28 is also electrically coupled to tag circuitry 62 which includes its own microprocessor 64 and memory 66 in the illustrative example. As indicated in FIG. 2, module 46 is electrically coupled to tag circuitry 62 and thus, module 46 and circuitry 62 are able to communicate with each other. In an alternative embodiment, button 60 is electrically coupled to tag circuitry 62 such that circuitry 62 notifies module 60 that button 60 has been pressed.

In some embodiments, module 46 is activated to convert voice inputs to text only while button 60 is pressed. In other embodiments, module 46 is activated in response to a first press of button 60 and then is deactivated in response to a second press of button 60. That is, sequential presses of button 60 activates and deactivates the voice-to-text function of module 46. In other embodiments, button 60 is omitted and module 46 of tag 28 becomes activated in response to one or more keywords being spoken into microphone 44. In such embodiments, module 46 becomes deactivated after a threshold amount of time elapses without any voice input being made into microphone 44 and/or in response to a deactivation keyword being spoken into microphone 44. The present disclosure also contemplates embodiments in which module 46 is activated using button 60 or using keywords. That is, the user is able to activate the voice-to-text function of module 46 using either method.

Tag 28 includes UWB communication circuitry 68 electrically coupled to tag circuitry 62 and operable to communicate bidirectionally with the UWB transceivers 26 of RTLS 24 in the FIG. 2 embodiment. Illustratively, UWB communication circuitry of tag 28 is in communication with three UWB transceivers of RTLS 24. Tag 28 also includes WiFi communication circuitry 102 electrically coupled to module 46 and operable to communicate with any of the WAP's 52 of system 10. Thus, circuitry 68, 102 each includes its own antenna for sending and/or receiving wireless messages or data according to the associated communication protocol. As indicated in FIG. 2, the tag ID is among the information transmitted by the UWB communication circuitry 68 to UWB transceivers 26 and text output by module 46 along with the tag ID is among the information transmitted by WiFi communication circuitry 102 to the WAP 52. It is contemplated, therefore, that circuitry 62 communicates the tag ID to module 46 so that module 46 is able to, in turn, transmit the tag ID along with the text.

The tag ID communicated to transceivers 26 from UWB communication circuitry 68 is provided to UWB computer 72 and then, ultimately, is stored in UWB RTLS server 70. Server 70 operates to correlate or associate the tag ID with the room ID in which tag 28 is located (or with any other location of tag 28 such as a hallway, pharmacy, laboratory, treatment room, etc. of the healthcare facility) and, in some embodiments, the tag ID and/or room ID are associated with a patient ID of the patient that is assigned to the room in which tag 28 is located. The text and tag ID communicated to one or more WAP's 52 is provided to the EMR server. The EMR server receives information regarding the room and/or patient ID's associated with the tag ID from UWB RTLS server 70. For example, EMR server 80 queries UWB RTLS server 70 to obtain the needed association data on a case-by-case basis in some embodiments. Alternatively or additionally, server 70 uploads its database of tag-to-room-to-patient associations to server 80 on a periodic basis. Thus, using the tag ID that accompanies the text arriving from one or more tags 28, the EMR server 80 is able to determine which patient EMR's are the ones in which the text transmitted by WiFi circuitry 102 of the respective one or more tags 28 are to be stored.

In some embodiments, a device such as computer 42, audio station 54, and/or patient support apparatus 14 that is located in the room 12 of the caregiver 20 using badge 28 to chart information to the respective patient's EMR, has a display screen on which the information being charted into the EMR is displayed as the caregiver speaks into microphone 44 after activation of the voice-to-text module. Thus, by viewing the display screen as the information is being charted, the caregiver 20 is able to confirm that the spoken information has been properly converted to text for storage in the patient's EMR. If incorrect information is shown on the display screen of the device, the caregiver can correct the information either via manually using an input device (e.g., keyboard, touch screen, etc.) to make the correction or by speaking replacement information into microphone 44 of badge 28 to overwrite the incorrect information in the EMR with the correct information.

In some embodiments having one or more vital signs monitors 40 in communication with EMR server 70, the vitals information is charted to the patient's EMR automatically in response to the caregiver 20 activating the voice-to-text module 46 of tag 28. Thus, in response to server 70 being notified that the caregiver 20 has activated module 46 of tag 28, server 70 queries the one or more vital signs monitors 40 in the respective room 12 via network 100 to obtain the vitals information from the respective monitors 40. In some embodiments, the automatically obtained vitals information is also displayed on the display screen of the device in room 12 so that the caregiver can verify that the vitals information charted to the patient's EMR is accurate and to make any corrections to the vitals information as desired. Alternatively or additionally, the EMR computer 50 at nurses station 32, or anywhere else where computer 50 may be located, is operable to display the information charted to the patient's EMR in response to the caregiver using tag 28.

Figure 3:
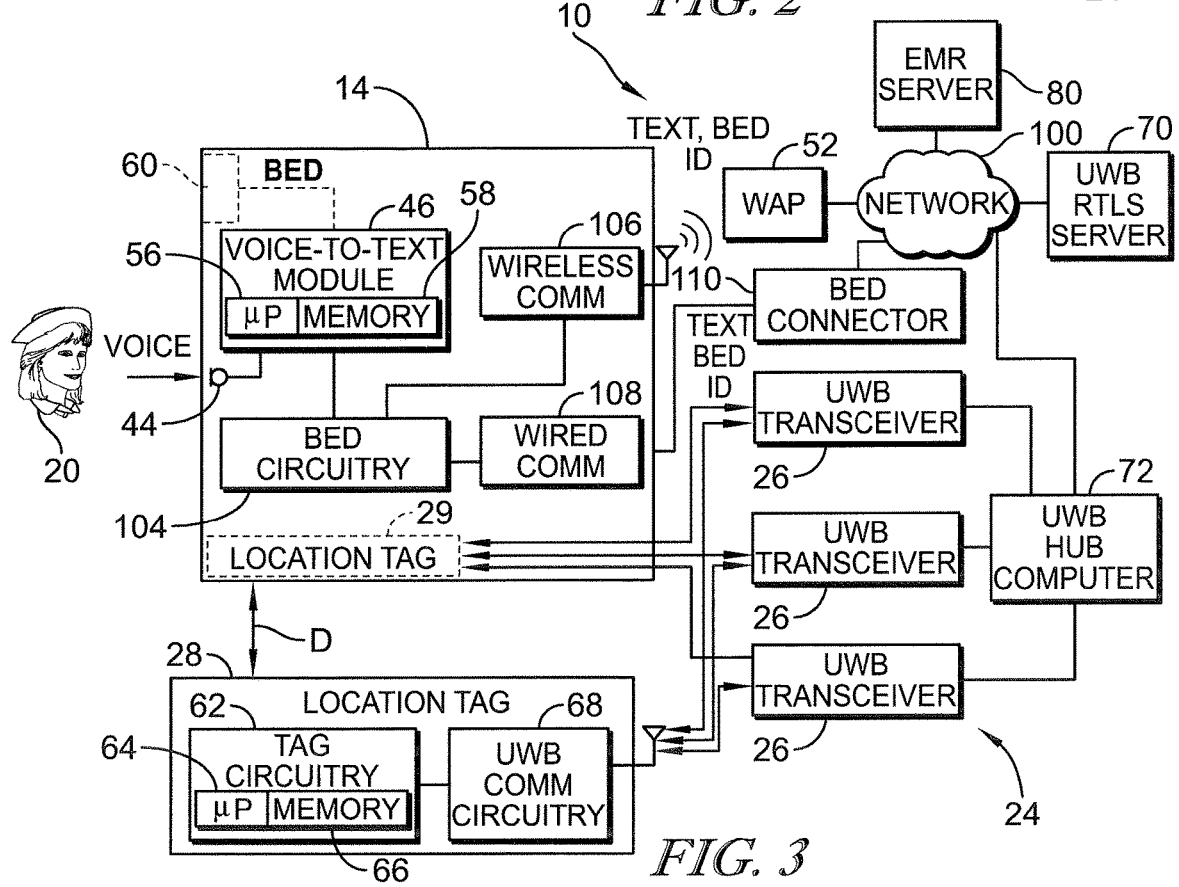
FIG. 3 is a block diagram of a second embodiment of a charting system showing the patient bed having a voice-to-text module, a microphone coupled to the voice-to-text module to receive a voice input from the caregiver, an optional user input (in phantom) on the patient bed to enable the voice-to-text module, WiFi communication circuitry coupled to the voice-to-text module operating to send text converted from the voice input from the caregiver by the voice-to-text module along with a bed ID to a wireless access point of the network for delivery to the EMR server for charting into a patient's electronic medical record, bed circuitry of the patient bed coupled to the voice-to-text module, the bed circuitry also being coupled to a bed connector via a wired communication port, the text and bed ID being alternatively or additionally transmitted by the bed circuitry to the network via the bed connector, the bed having a location tag communicating wirelessly with three UWB transceivers that, in turn, are coupled to the UWB hub computer, and a second location tag spaced from the patient bed to enable the voice-to-text module when within a threshold distance, D, of the patient bed, and the second location tag communicating wirelessly with the three UWB transceivers.

Referring now to FIG. 3, an embodiment is shown diagrammatically in which bed 14 includes voice-to-text module 46 which, in turn, includes microprocessor 56 and memory 58 that operate in substantially the same manner as described above in connection with FIG. 2. Thus, microprocessor 56 executes voice-to-text software stored in memory 58 in response to module 46 being activated or enabled in response to the user input 60 being pressed, if embodied as a button 60, or selected on a display screen, if embodied as a selectable button or icon 60, or in response to one or more keywords being spoken into microphone 44 of bed 14.

In the FIG. 3 example, module 46 is electrically coupled to bed circuitry 104 which is, in turn, coupled electrically to wireless communication circuitry 106 and wired communication circuitry 108 of bed 14. Thus, text data is output from module 46 to bed circuitry 104 which then uses wireless communication circuitry 106 to transmit the text data and a bed ID to one or more of the wireless access points 52 in some embodiments. Optionally, other types of bed data (e.g., caster brake status, siderail position, patient weight as sensed by load cells of a weigh scale system of bed 14, status of a bed exit or patient position monitoring system that also may rely on signals from load cells of bed 14, an angle at which a head section of a mattress support deck of bed 14 is raised from horizontal, and the like) is also transmitted from wireless communication circuitry 106 to wireless access point(s) 52 along with the text data and bed ID or in separate transmissions. The bed status data is stored in the nurse call server 78 and/or the EMR server 80 and, if desired, is displayed at the nurse call computer 30, for example. The text data is stored in the EMR server 80.

In other embodiments, wireless communication circuitry like circuitry 102 of FIG. 2 is included in bed 14 of FIG. 3 and is directly electrically coupled to module 46. Thus, it is contemplated that bed status data is transmitted from bed 14 via circuitry 104 and text data and the bed ID are transmitted separately from bed 14 via circuitry 102 in some embodiments. In a further variant, circuitry 104 is omitted and the bed status data is communicated from bed circuitry 104 to module 46 which then uses circuitry 102 to transmit the bed status data wirelessly, either separately from the text data and bed ID or together with the text data and bed ID. When bed status data is transmitted separately from the text data by circuitry 106 or, if present, circuitry 102, the bed ID is also included as part of the bed status data in some embodiments.

Still referring to FIG. 3, wired communication circuitry 108 of bed 14 is coupled by a wired connection, such as with a 37-pin connector cable, to a bed connector 110 which is typically mounted at a fixed location to a wall of the patient room 12 or to an architectural product such as a headwall unit which is, in turn, mounted to a wall of the patient room. Bed status data, including the bed ID, is transmitted from circuitry 108 of bed 14 to the bed connector 110 and then on to the nurse call server 78 and/or the EMR server 80 and/or the RTLS server 70 via network 100. In some embodiments, bed connector 110 comprises a bed interface unit (BIU) or a network interface unit (NIU) of the type shown and described in U.S. Pat. Nos. 7,538,659 and 7,319,386 and in U.S. Patent Application Publication Nos. 2009/0217080, 2009/0212925 and 2009/0212926, each of which is hereby expressly incorporated by reference herein in its entirety. In other embodiments, bed connector 110 comprises a communications hub of the type shown and described in U.S. Patent Application Publication No. 2017/0323555 which is hereby incorporated by reference herein in its entirety.

The bed connector 110 has a location ID that is transmitted along with the bed status data in some embodiments. The location ID of the bed connector 110 is correlated with the room location in a database stored in RTLS server 70. Thus, the bed ID and location ID are correlated with each other based on data sent from circuitry 108 of bed and from bed connector 110 and the text and bed ID are correlated with each other in the EMR server 80 based on data sent from circuitry 106 of bed 14. Communication between servers 70, 80 allows EMR server to determine the room location that corresponds with the bed ID and text and with a particular patient assigned to the room.

As indicated in FIG. 3, the text data from voice-to-text module 46 is also provided to bed circuitry 104 and transmitted from wired communication circuitry 108 to the bed connector 110 and on to one or more of servers 70, 78, 80 via network 100 in certain circumstances. For example, if wireless communication circuitry 106 on bed 14 fails, then communication of the text data from voice-to-text module 46 via the wired communication circuitry 108 is used as a back-up communication channel. As another example, if wireless communication circuitry 106 is not in communication with any wireless access point 52 for whatever reason, then communication of the text data from voice-to-text module 46 via the wired communication circuitry 108 is used as a back-up communication channel.

It should be appreciated that circuitry 104 of beds 14 used in healthcare facilities is typically quite complex and, depending upon the type of bed 14, may include a number of circuit boards or modules that are in electrical communication with each other to form an on-bed network and that are configured for carrying out the various bed functions such as movement of deck articulation actuators to move a mattress support deck into various positions and configurations, movement of lift system actuators to raise and lower an upper frame that carries the mattress support deck relative to a base frame of the bed, operation of a pneumatic system to inflate and deflate various air cells or bladders included in the mattress, operation of a bed exit and/or patient position monitoring system of the bed, operation of a weigh scale system of the bed, operation of a motorized propulsion system of the bed, operation of a power management system to convert standard AC power into various DC voltages for powering various components of the bed circuitry, and so forth. Examples of beds 14 having such bed circuitry including networked modules can be found in U.S. Pat. Nos. 5,715,548 and 7,296,312 and in U.S. Patent Application Publication No. 2018/0161225, each of which is hereby incorporated by reference herein for all that it teaches.

Optionally, bed 14 has an equipment tag 29 attached thereto as shown (in phantom) in FIG. 3. In the illustrative example, tag 29 is in communication with three UWB transceivers 26 which, in turn, are in communication with UWB hub computer 72 which communicates with UWB RTLS server 70 via network 100. Tag 28 of the caregiver 20 is also shown in FIG. 3 and includes tag circuitry 62 which has its own microprocessor 64 and memory 66 similar to that of the tag 28 shown in FIG. 2. Tag 28 of FIG. 3 also has UWB communication circuitry 68 like that of tag 28 of FIG. 2. Thus, the description above of these components of tag 28 in connection with FIG. 2 is equally applicable to the tag 28 shown in FIG. 3. Tag 29 on bed 14 also has circuitry 62 with microprocessor 64 and memory 66 and also has UWB communication circuitry 68 but these are simply not illustrated in FIG. 3 to save space. Illustratively, tag 28 is also in communication with the three UWB transceivers 46 of the RTLS system 24 of FIG. 3.

If bed 14 has tag 29 coupled thereto, then the location of bed 14 is determined by RTLS 24 using the wireless communications between tag 29 and transceivers 26 such that the location ID of bed connector 110 need not be used in connection with correlating the room number to the bed ID. In such embodiments having tag 29 on bed 14, therefore, bed connector 110 can be omitted such that no wired connection between bed 14 and network 100 is needed, although typically bed 14 will still have a power cord with a power plug that plugs into a standard AC power outlet while bed 14 is located within the respective room 12.

The tag ID communicated to transceivers 26 from tags 28, 29 is provided to UWB computer 72 and then, ultimately, is stored in UWB RTLS server 70. Server 70 operates to correlate or associate the tag ID's of tags 28, 29 with the room ID in which tags 28, 29 are located (or with any other location such as a hallway, pharmacy, laboratory, treatment room, etc. of the healthcare facility) and, in some embodiments, the tag ID of tag 29 and/or room ID are associated with a patient ID of the patient that is assigned to the room in which bed 14 with tag 29 is located. Of course the tag ID of tag 29 is correlated with the bed ID as noted above. The text and bed ID communicated to one or more WAP's 52 and/or to bed connector 110 is provided to the EMR server 80. The EMR server 80 receives information regarding the room and/or patient ID's associated with the tag ID's of tags 28, 29 from UWB RTLS server 70. For example, EMR server 80 queries UWB RTLS server 70 to obtain the needed association data on a case-by-case basis in some embodiments. Alternatively or additionally, server 70 uploads its database of tag-to-room-to-patient associations to server 80 on a periodic basis. Thus, using the bed ID's that accompanies the text arriving from one or more beds 14, the EMR server 80 is able to determine which patient EMR's are the ones in which the text transmitted by circuitry 106 and/or circuitry 108 of the various beds 14 are to be stored.

In some embodiments contemplated by this disclosure, the voice-to-text module 46 of bed 14 is activated in response to the tag 28 of caregiver 20 being within a threshold distance, D, of tag 29 of bed 14. The activation of module 46 due to proximity of tag 28 with tag 29 within distance D, which may be on the order of about three to about five feet (about 91.44 cm to about 152.4 cm) in some embodiments, is an alternative to the use of button 60 on bed 14 or the use of spoken keywords to activate module 46. Distance D is less than about three feet or is more than about five feet in other embodiments.

In an alternative embodiment, the use of button 60 or spoken keywords is only able to activate module 46 if tag 28 of an authorized caregiver 20 is determined to be within distance D of tag 29 by RTLS 24. Thus, RTLS system 24 initiates a message to bed 14 via network 100 to indicate the detection of the threshold proximity of an authorized caregiver 20 to bed 14 to thereby permit EMR charting using module 46. The authorized caregiver 20 in proximity to bed 14 is then able to activate module 46 using button 60 or by speaking keywords as the case may be. In other instances when an authorized caregiver 20 is not within the threshold proximity of bed 14, then pressing button 60 or speaking keywords into microphone 44 does not result in activation of module 46. Thus, the patient 18 or a visitor would not be able to activate module 46 for EMR charting purposes if an authorized caregiver 20 is not present in the room 12 and located within the threshold distance D between tags 28, 29.

In some embodiments, in response to an unauthorized user, such as the patient or a visitor, attempting to activate module 46 for EMR charting, an alert message is sent from bed 14 to nurse call server 78 for display on nurse call computer 30 at master nurse station 32 and/or for communication to a portable wireless communication device (e.g., a smart phone or wireless handset or pager) of a caregiver 20 assigned to the room 12 where the attempted unauthorized use of module 46 occurred or is occurring. Other alerts, such as displaying a message on a graphical user interface of bed 14, announcing a voice alert message using a speaker on bed 14, lighting up a portion of a dome light (e.g., an indicator light located in a hallway outside the patient room 12 adjacent a door of the room 12), displaying a message on EMR computer 50, and so forth are also contemplated by the present disclosure in response to an attempted unauthorized use of module 46 of bed 14 for EMR charting.

In some embodiments, module 46 is activated to convert voice inputs to text only while button 60 of bed 14 is pressed. In other embodiments, module 46 is activated in response to a first press of button 60 on bed 14 and then is deactivated in response to a second press of button 60 on bed 14. Thus, sequential presses of button 60 activates and deactivates the voice-to-text function of module 46. Selection of button 60 on a touchscreen display of bed 14 is also considered to be a "press" of the button 60 for discussion purposes herein. In other embodiments, button 60 is omitted from bed 14 and module 46 becomes activated in response to one or more keywords being spoken into microphone 44 of bed 14. In such embodiments, module 46 becomes deactivated after a threshold amount of time elapses without any voice input being made into microphone 44 and/or in response to a deactivation keyword being spoken into microphone 44. The present disclosure also contemplates embodiments in which module 46 of bed 14 is activated using button 60 or using keywords. That is, the user is able to activate the voice-to-text function of module 46 of bed 14 using either method.

In some embodiments, a device such as computer 42, audio station 54, and/or patient support apparatus 14 that is located in the room 12 of the caregiver 20 using bed 14 to chart information to the respective patient's EMR, has a display screen on which the information being charted into the EMR is displayed as the caregiver speaks into microphone 44 after activation of the voice-to-text module. Thus, by viewing the display screen as the information is being charted, the caregiver 20 is able to confirm that the spoken information has been properly converted to text for storage in the patient's EMR. If incorrect information is shown on the display screen of the device, the caregiver can correct the information either via manually using an input device (e.g., keyboard, touch screen, etc.) to make the correction or by speaking replacement information into microphone 44 of bed 14 to overwrite the incorrect information in the EMR with the correct information.

In some embodiments having one or more vital signs monitors 40 in communication with EMR server 70, the vitals information is charted to the patient's EMR automatically in response to the caregiver 20 activating the voice-to-text module 46 of bed 14. Thus, in response to server 70 being notified that the caregiver 20 has activated module 46 of bed 14, server 70 queries the one or more vital signs monitors 40 in the respective room 12 via network 100 to obtain the vitals information from the respective monitors 40. In some embodiments, the automatically obtained vitals information is also displayed on the display screen of the device in room 12 so that the caregiver can verify that the vitals information charted to the patient's EMR is accurate and to make any corrections to the vitals information as desired. Alternatively or additionally, the EMR computer 50 at nurse's station 32, or anywhere else where computer 50 may be located, is operable to display the information charted to the patient's EMR in response to the caregiver using module 46 of bed 14.

Figure 4:
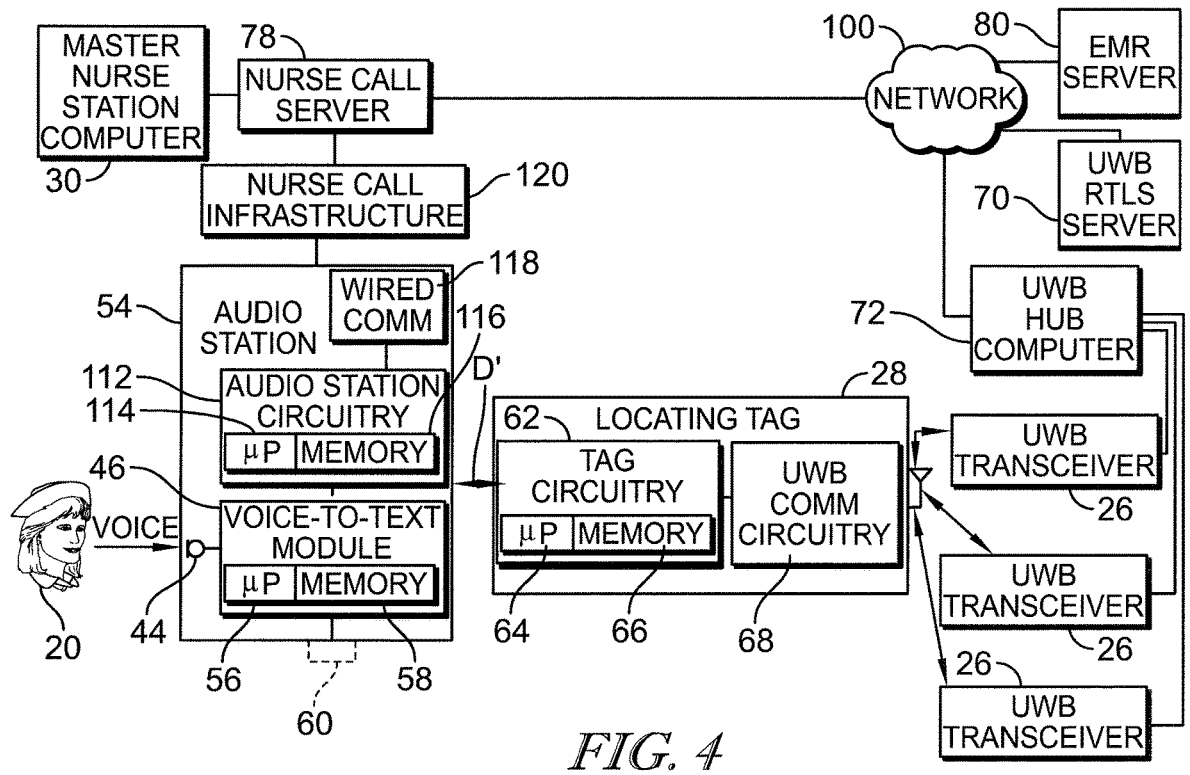
FIG. 4 is a block diagram of a third embodiment of a charting system showing the audio station having a voice-to-text module coupled to audio station circuitry which is, in turn, coupled to nurse call infrastructure via a wired communication port, a microphone coupled to the voice-to-text module to receive a voice input from the caregiver, the voice-to-text module and audio station circuitry operating to send text converted from the voice input from the caregiver by the voice-to-text module to a nurse call server via the wired communication port and nurse call infrastructure for delivery to the EMR server for charting into a patient's electronic medical record, and a locating tag spaced from the audio station to enable the voice-to-text module when within a threshold distance, D, of the audio station, and the locating tag communicating wirelessly with three UWB transceivers that are, in turn, in communication with a UWB hub computer and a UWB server.

Referring now to FIG. 4, an embodiment is shown diagrammatically in which audio station 54 includes voice-to-text module 46 which, in turn, includes microprocessor 56 and memory 58 that operate in substantially the same manner as described above in connection with FIGS. 2 and 3. Thus, microprocessor 56 executes voice-to-text software stored in memory 58 in response to module 46 of audio station 54 being activated or enabled based on the user input 60 being pressed, if embodied as a button 60, or selected on a display screen, if embodied as a selectable button or icon 60, or based on one or more keywords being spoken into microphone 44 of audio station 54. Voice-to-text module 46 is coupled electrically to audio station circuitry 112 of audio station 54. Circuitry 112 includes a microprocessor 114 and memory 116. Thus, microprocessor 114 executes software stored in memory 116 to provide the nurse call system functionality of audio station 54.

In the FIG. 4 example, module 46 is electrically coupled to audio station circuitry 112 which is, in turn, coupled electrically to wired communication circuitry 118. Thus, text data is output from module 46 to circuitry 112 which transmits the text and an audio station ID to nurse call server 78 via wired communication circuitry 118. In the illustrative embodiment, nurse call infrastructure 120 such as CAT-5 cabling, routers, or the like is used to interconnect audio station 54 with nurse call server 78. Nurse call server 78 transmits the text data received from audio station 54 to EMR server 80 for storage in the medical record of the patient 18 that is assigned to the room 12 having audio station 54.

In some embodiments, wireless communication circuitry like circuitry 102 of FIG. 2 is included in audio station 54 of FIG. 4 and is directly electrically coupled to module 46. Thus, it is contemplated that text data and the audio station ID is transmitted from audio station 54 wirelessly via circuitry 102 for receipt by one or more wireless access points 52 in some embodiments. In some such embodiments, module 46 is not electrically coupled to audio station circuitry 112 but operates as a completely separate component of audio station 54. Having module 46 electrically decoupled from circuitry 112 within audio station 54 prevents any errors that may occur in module 46 from possibly interfering with the core nurse call functionality of circuitry 112 of audio station 54. Thus, having module 46 and circuitry 112 completely isolated from each other on a hardware basis may be beneficial in connection with meeting the UL-1069 standard of Underwriter's Laboratory for nurse call systems. Additional details of audio station 54 and other components of nurse call systems are shown and described in U.S. Pat. Nos. 8,598,995; 8,384,526; 8,169,304; 8,046,625; 7,746,218; 7,538,659; 7,319,386; 7,242,308; 6,897,780; 6,362,725; 6,147,592; 5,838,223; 5,699,038 and 5,561,412, all of which are hereby incorporated by reference herein in their entirety to the extent that they are not inconsistent with the present disclosure which shall control as to any inconsistencies.

As mentioned above, the audio station 54 has an audio station ID that is transmitted along with the text data in some embodiments. The audio station ID of the audio station 54 is correlated with the room number in a database stored in RTLS server 70. Thus, the audio station ID and location are correlated with each other based on data sent from circuitry 118 of audio station 54 and the text and audio station ID and/or room number are correlated with each other in the EMR server 80 after nurse call server 78 transmits the text and room data received from the audio station 54 to EMR server 80 over the network 100. Communication between servers 78, 80 allows EMR server 80 to determine the room location that corresponds with the audio station ID and text and with a particular patient assigned to the room 12 in which the audio station 54 is located.

In some embodiments contemplated by this disclosure, the voice-to-text module 46 of audio station 54 is activated in response to the tag 28 of caregiver 20 being within a threshold distance, D', of audio station 54. Unlike bed 14 which is a piece of mobile medical equipment that can be transported to various locations throughout the healthcare facility, audio station 54 is mounted at a fixed, known location in the healthcare facility. Thus, audio station 54 does not need to have an equipment tag 29 like bed 14 does in order for RTLS server 70 to determine the location of the audio station 54. Therefore, in some embodiments, RTLS server 70 has software that models the floorplan of the healthcare facility and has zones determined by certain X and Y coordinates relative to origin 82 (see FIG. 1) that are defined around the known X,Y coordinates of each of the audio stations 54 using a radius of D'. Accordingly, RTLS server 70 is able to determine whether any caregiver tags 28 are within the zone defined by radius D'.

Still referring to FIG. 4, locating tag 28 includes tag circuitry 62 having microprocessor 64 and memory 66 and also includes UWB communication circuitry 68. The description above of these components of tag 28 in connection with FIGS. 1-3 is equally applicable to the embodiment of FIG. 4. Illustratively, tag 28 shown in FIG. 4 is in communication with the three UWB transceivers 26 which are, in turn, in communication with UWB RTLS server 70 via UBW hub computer 72 and network 100. The above descriptions of server 70 and computer 72 is equally applicable to the embodiment of FIG. 4.

After server 70 determines that caregiver tag 28 is within distance D' of audio station 54, server 70 sends a message to nurse call server 78 which, in turn, sends an activation message for receipt by voice-to-text module 46 of audio station 54 to activate or enable the module 46. In the illustrative example, the activation message is sent to voice-to-text module via infrastructure 120, communication circuitry 118, and audio station circuitry 116 of the audio station 54. Once activated, module 46 receives voice inputs from the caregiver 20 via microphone 44 and converts the voice inputs to text for storage in the EMR of the patient 18 in the room 12 having audio station 54. The activation of module 46 due to proximity of tag 28 within distance D' of the audio station 54, which may be on the order of about three to about five feet (about 91.44 cm to about 152.4 cm) in some embodiments, is an alternative to the use of button 60 on audio station 54 or the use of spoken keywords to activate module 46. Distance D' is less than about three feet or is more than about five feet in other embodiments.

In an alternative embodiment, the use of button 60 or spoken keywords is only able to activate module 46 of audio station 54 if tag 28 of an authorized caregiver 20 is determined to be within distance D' of audio station 54 by RTLS 24. Thus, RTLS 24 initiates a message to audio station 54 to indicate the detection of the threshold proximity of an authorized caregiver 20 to audio station 54 to thereby permit activation of module 46 of audio station 54. The authorized caregiver 20 in proximity to audio station 54 is then able to activate module 46 using button 60 or by speaking keywords as the case may be. In other instances when an authorized caregiver 20 is not within the threshold proximity of audio station 54, then pressing button 60 or speaking keywords into microphone 44 does not result in activation of module 46. Thus, the patient 18 or a visitor would not be able to activate module 46 of audio station 54 for EMR charting purposes if an authorized caregiver 20 is not present in the room 12 and located within the threshold distance D' of audio station 54.

In some embodiments, in response to an unauthorized user, such as the patient or a visitor, attempting to activate module 46 of audio station 54 for EMR charting, an alert message is sent from audio station 54 to nurse call server 78 for display on nurse call computer 30 at master nurse station 32 and/or for communication to a portable wireless communication device (e.g., a smart phone or wireless handset or pager) of a caregiver 20 assigned to the room 12 where the attempted unauthorized use of module 46 occurred or is occurring. Other alerts, such as displaying a message on a graphical user interface of bed 14, announcing a voice alert message using a speaker on bed 14, lighting up a portion of a dome light (e.g., an indicator light located in a hallway outside the patient room 12 adjacent a door of the room 12), displaying a message on EMR computer 50, and so forth are also contemplated by the present disclosure in response to an attempted unauthorized use of module 46 of audio station 54 for EMR charting.

In some embodiments, module 46 is activated to convert voice inputs to text only while button 60 of audio station 64 is pressed. In other embodiments, module 46 is activated in response to a first press of button 60 on audio station 54 and then is deactivated in response to a second press of button 60 on audio station. Thus, sequential presses of button 60 activates and deactivates the voice-to-text function of module 46. Selection of button 60 on a touchscreen display of audio station 54 is also considered to be a "press" of the button 60 for discussion purposes herein. In other embodiments, button 60 is omitted from audio station 54 and module 46 becomes activated in response to one or more keywords being spoken into microphone 44 of bed 14. In such embodiments, module 46 of audio station 54 becomes deactivated after a threshold amount of time elapses without any voice input being made into microphone 44 and/or in response to a deactivation keyword being spoken into microphone 44. The present disclosure also contemplates embodiments in which module 46 of audio station 54 is activated using button 60 or using keywords. That is, the user is able to activate the voice-to-text function of module 46 of audio station 54 using either method.

In some embodiments, a device such as computer 42, audio station 54, and/or patient support apparatus 14 that is located in the room 12 of the caregiver 20 using audio station 54 to chart information to the respective patient's EMR, has a display screen on which the information being charted into the EMR is displayed as the caregiver speaks into microphone 44 after activation of the voice-to-text module 46. Thus, by viewing the display screen as the information is being charted, the caregiver 20 is able to confirm that the spoken information has been properly converted to text for storage in the patient's EMR. If incorrect information is shown on the display screen of the device, the caregiver can correct the information either via manually using an input device (e.g., keyboard, touch screen, etc.) to make the correction or by speaking replacement information into microphone 44 of audio station 54 to overwrite the incorrect information in the EMR with the correct information.

In some embodiments having one or more vital signs monitors 40 in communication with EMR server 70, the vitals information is charted to the patient's EMR automatically in response to the caregiver 20 activating the voice-to-text module 46 of audio station 54. Thus, in response to server 70 being notified that the caregiver 20 has activated module 46 of audio station 54, server 70 queries the one or more vital signs monitors 40 in the respective room 12 via network 100 to obtain the vitals information from the respective monitors 40. In some embodiments, the automatically obtained vitals information is also displayed on the display screen of the device in room 12 so that the caregiver can verify that the vitals information charted to the patient's EMR is accurate and to make any corrections to the vitals information as desired. Alternatively or additionally, the EMR computer 50 at nurse's station 32, or anywhere else where computer 50 may be located, is operable to display the information charted to the patient's EMR in response to the caregiver using module 46 of audio station 54.

Figure 5:
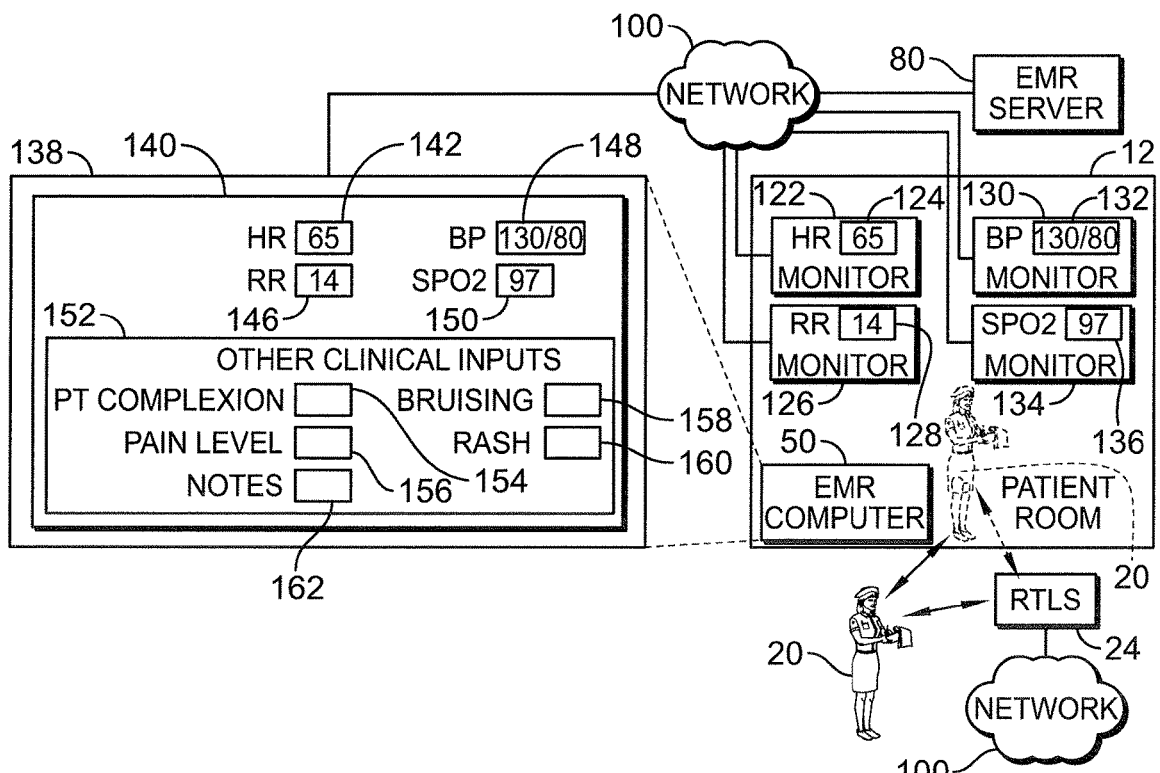
FIG. 5 is a block diagram of a fourth embodiment of a charting system showing a RTLS tracking a caregiver's location, a patient room having an EMR computer and having four vital signs monitors to monitor, respectively, heart rate, respiration rate, blood pressure, and pulse oximetry, the four vital signs monitors being coupled to an EMR server via a network, data from the four vital signs monitor being charted automatically to the EMR server in response to the caregiver entering the patient room (as shown in phantom), an enlarged image of a display screen of the EMR computer showing the data from the four vital signs monitors in respective data boxes to indicate that the data has been charted to the EMR server, and the display screen also having an "other clinical inputs" window having a menu of other clinical inputs that the caregiver may choose to populate via voice or text inputs to the EMR computer.

Referring now to FIG. 5, an embodiment is shown of a charting system in which EMR computer 50 is located in the patient room 12. In FIG. 5, rather than depicting a generic vital sign monitor 40 like is shown in FIG. 1, four specific vital sign monitors are shown diagrammatically. In particular, a heart rate (HR) monitor 122 has a display 124 in which a patient's measured heart rate is shown, a respiration rate (RR) monitor 126 has a display 128 in which the patient's measured respiration rate is shown, a blood pressure (BP) monitor has a display 132 in which the patient's measured blood pressure is shown, and a pulse oximeter (aka an SpO2 monitor) 134 has a display 136 in which the patient's pulse oximetry data is shown.

As indicated in FIG. 5, each of monitors 122, 126, 130, 134 is communicatively coupled to EMR server 80 via network 100. The communication links between monitors 122, 126, 130, 134 and EMR server 80 include wired and/or wireless communication links. In response to RTLS system 24 detecting entry of caregiver 20 into room 12 of FIG. 5, the vitals data shown on screens 124, 128, 132, 136 of respective monitors 122, 126, 130, 134 is automatically charted into the patient's EMR for storage in EMR server 80. RTLS 24 is depicted as a single block in FIG. 5 but it should be appreciated that RTLS 24 includes receivers 26 or transceivers 26, badges 28, server 80 and, in some embodiments, UWB hub computer 72 as has been described above in connection with various RTLS 24 embodiments. Thus, it should also be appreciated that caregiver 20 of FIG. 5 is wearing a badge 28 that is detected moving from outside room 12 into room 12.

In some embodiments, RTLS server 70 notifies EMR server 80 that the caregiver 20 has entered room 12 and, in response to the notification, EMR server 80 sends a message to monitors 122, 126, 130, 134 commanding the monitors 122, 126, 130, 134 to transmit the current vitals readings, shown on screens 124, 128, 132, 136 in the illustrative example, to the EMR server 80. After receiving the vitals information from monitors 122, 126, 130, 134 and storing it in the respective patient's EMR, server 80 transmits the stored vitals information received from monitors 122, 126, 130, 134 to the EMR computer 50 located in the room with the patient 18 and caregiver 20.

In the illustrative FIG. 5 embodiment, EMR computer 50 in room 12 has a display screen 138 on which a window 140 is shown in response to receipt of the vitals information from EMR server 80. Window 140 has an HR field 142 in which the measured heart rate from monitor 122 is displayed, an RR field 146 in which the measured respiration rate from monitor 126 is displayed, a BP field 148 in which the measured blood pressure from monitor 130 is displayed, and an SPO2 field in which the measured pulse oximetry data is shown. As is apparent in FIG. 5, the numerical values in each of fields 142, 146, 148, 150 matches the numerical data shown on screens 124, 128, 132, 136 of respective monitors 122, 126, 130, 134. Thus, by viewing screen 138 of EMR computer 50 and comparing the numerical data in fields 142, 146, 148, 150 with the numerical data shown on respective screens 124, 128, 132, 136, the caregiver 20 is able to confirm that the vitals information has been accurately charted automatically into the patient's EMR.

If the caregiver 20 notices a mismatch or other error in the vitals information shown in window 140 of screen 138, the caregiver 20 is able to use computer 50 to make any needed changes or corrections to the data in fields 142, 146, 148, 150. For example, using a keyboard of computer 50 the caregiver 20 can navigate to the desired field 142, 146, 148, 150 using the tab key or arrow keys and then edit the vitals information within the selected field 142, 146, 148, 150. Alternatively or additionally, the caregiver 20 can use of mouse of computer 50 and click on the desired filed 142, 146, 148, 150 in which changes or corrections are to be made using the keyboard. Further alternatively or additionally, if screen 138 is a touchscreen, the caregiver 20 can touch the desired field 142, 146, 148, 150 to select it for subsequent editing with the keyboard of computer 50.

At the bottom of window 140 beneath fields 142, 146, 148, 150, an "other clinical inputs" window 152 is displayed on display screen 138 of EMR computer 50. Window 152 includes a patient complexion field 154 in which information about the patient's complexion can be entered by the caregiver 20, a pain level field 156 in which information about the patient's pain level (e.g., on a scale of 1-10) can be entered by the caregiver 20, a bruising field 158 in which information about any bruises on the patient 18 can be entered by the caregiver 20, a rash field 160 in which information about any rashes on the patient 18 can be entered by the caregiver 20, and a notes field 162 in which any other miscellaneous notes that the caregiver 20 may wish to store in the patient's EMR can be entered by the caregiver. In other embodiments, additional or different clinical inputs fields are included in window 152 at the discretion of the system designer or programmer. The names of fields 154, 156, 158, 160 serves as a reminder to the caregiver 20 as to the types of other clinical inputs that can be entered into the patient's EMR, as desired. Fields 154, 156, 158, 160, 162 are selected and edited in any of the manners described above, such as in connection with fields 142, 146, 148, 150.

Optionally, the EMR computer 50 in the FIG. 5 embodiment includes voice-to-text module 46 like those described above in connection with FIGS. 1-4. In such embodiments, the caregiver 20 activates the voice-to-text module of computer 50 using a button of computer 50 or an icon on screen 138 and provides voice input into the microphone 44 of computer 50 to edit or populate fields 142, 146, 148, 150, 154, 156, 158, 160, 162 with information to be charted to the patient's EMR. To navigate from field-to-filed, the caregiver 20 speaks appropriate keywords, such as the name of the particular field 142, 146, 148, 150, 154, 156, 158, 160, 162.

The vocally selected field 142, 146, 148, 150, 154, 156, 158, 160, 162 becomes highlight on screen 138 to let the caregiver 20 know that voice inputs for the selected field can then be spoken.

After the fields 142, 146, 148, 150, 154, 156, 158, 160, 162 shown on screen 138 of EMR computer 50 are populated with new or modified information regarding the patient's vitals and other clinical inputs, the caregiver 20 takes an action to chart the new and/or modified information into the patient's EMR. For example, the caregiver speaks one or more charting keyword (e.g., "chart to patient record") into the microphone 44 of computer 50 while the voice-to-text module 46 is activated and computer 50 responds by sending the vitals information and other clinical inputs appearing in fields 142, 146, 148, 150, 154, 156, 158, 160, 162 of screen 138 to the EMR server 80 for storage in the patient's EMR. Alternatively or additionally, a charting button is provided on the keyboard of computer 50 (e.g., one of the F1-F12 buttons is designated as being the charting button) or on the display screen 138 for selection by the caregiver 20 to cause computer 50 to send the vitals information and other clinical inputs appearing in fields 142, 146, 148, 150, 154, 156, 158, 160, 162 of screen 138 to the EMR server 80 for storage in the patient's EMR. In FIG. 5, a diagrammatic line interconnects display screen 138 with network 100. That diagrammatic line is intended to represent the communication link between computer 50 and network 100.

The discussion above of EMR computer 50 located in room 12, including having display screen 138 with windows 140, 152 including fields 142, 146, 148, 150, 154, 156, 158, 160, 162, is equally applicable to any room computer 42 (FIG. 1) that may be included in room 12. That is, it is contemplated by this disclosure that any computer 42 in room 12 may be equipped with the software and/or hardware (e.g., voice-to-text algorithm software and/or voice-to-text module 46) that was described above in connection with FIG. 5 as being included in EMR computer 50. Furthermore, screen 138 with windows 140, 152 having fields 142, 146, 148, 150, 154, 156, 158, 160, 162, as well as the variants discussed above in connection with FIG. 5, is exemplary of screens that may appear on bed 14 and audio station 54 for EMR charting purposes.

Figure 6:
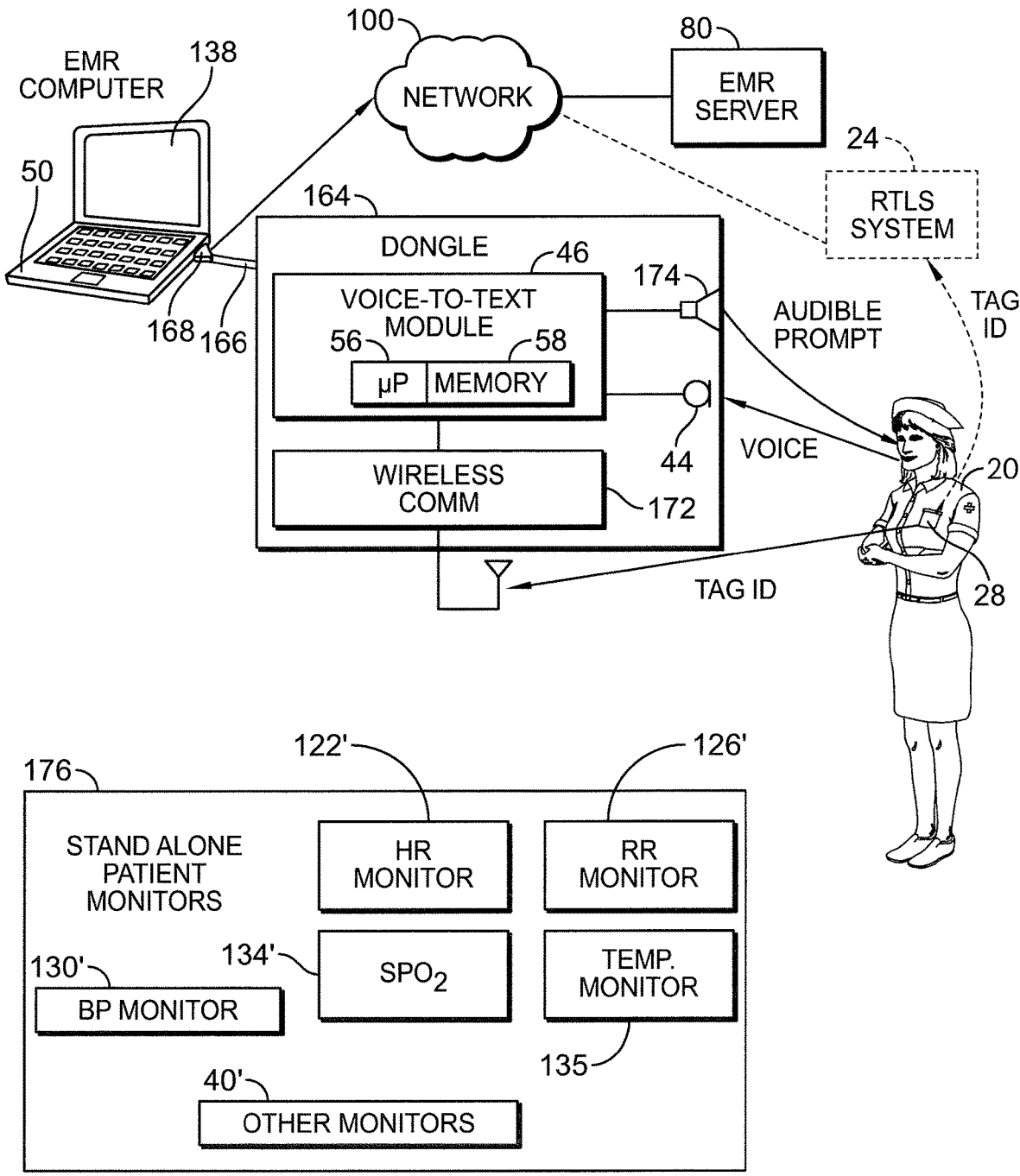
FIG. 6 is a block diagram of a fifth embodiment of a charting system showing stand-alone patient monitors including monitors for heart rate, respiration rate, pulse oximetry, temperature, and other monitors and showing a dongle coupled to an EMR computer which is, in turn, coupled to an EMR server via a network, the dongle having wireless communication circuitry to detect presence of a caregiver location tag, a voice-to-text module coupled to a speaker to provide an audible prompt to the caregiver to chart data from the stand-alone patient monitors into a patient electronic medical record stored in the EMR server in response to detecting the presence of the caregiver location tag, a microphone coupled to the voice-to-text module to receive voice inputs from the caregiver of the data from the stand-alone patient monitors, and showing an RTLS system (in phantom) receiving a tag ID from the caregiver location tag as an alternative to the dongle detecting the caregiver location tag.

Referring now to FIG. 6, an embodiment is shown in which a dongle 164 is electrically coupled to EMR computer 50 such as by plugging in a connector 168 at an end of a cable 166 of the dongle 164 into a port of the computer 50. For example, the port and connector 168 are a Universal Serial Bus (USB) port and connector in some embodiments. Dongle 164 includes voice-to-text module 46 having microprocessor 56 and memory 58. Thus, use of dongle 164 is one way of equipping EMR computer 50 with voice-to-text module 46. Accordingly, dongle 164 may be coupled to the EMR computer 50 of the FIG. 5 embodiment in a variant of that embodiment, if desired.

Still referring to FIG. 6, dongle 164 has wireless communication circuitry 172 that is electrically coupled to voice-to-text module 46. Wireless circuitry 172 is configured to detect presence of the caregiver location tag 28 such as by receipt of the tag ID transmitted from the tag 28 worn by the caregiver 28. It is contemplated by this disclosure that circuitry 172 uses IR technology or short range wireless communication technology so that only tags 28 that are within the same room 12 as dongle 164 are detected by circuitry 172. In response to detection of the caregiver tag 28 by circuitry 172, the voice-to-text module 46 plays an audible prompt using a speaker 174 included in dongle 164.

The audible prompt includes a message instructing the caregiver 20 to chart vitals data and other clinical inputs, as desired, into the patient's EMR. The caregiver then speaks into microphone 44 of dongle 44 to provide the data and other inputs for charting to the patient's EMR.

In the illustrative embodiment, detection of tag 28 by circuitry 172 of dongle 164 results in voice-to-text module 46 being activated (aka enabled or turned on) without the need for the caregiver to take any further action such as pressing a button (e.g., button 60 described above) of dongle 164 or speaking one or more keywords to activate the module 46 of dongle 164. In other embodiments, dongle 164 includes a button, like button 60, that is electrically coupled to module 46 and that is pressed to activate module 46. Alternatively or additionally, module 46 of dongle 164 is activated in response to the caregiver 20 speaking one or more activation keywords into the microphone 44 of dongle 164.

After module 46 of dongle 164 is activated and the audible prompt is played through speaker 174, spoken inputs by the caregiver 20 into microphone 44 of dongle 164 are input into module 47 and converted to text that is transmitted from dongle 164 via cable 166 and connector 168 to EMR computer 50 and then on to network 100 for ultimate delivery to EMR server 80 for storage in the patient's EMR. In the embodiment of FIG. 6, a set of standalone patient monitors 176 are present in the patient room 12 along with dongle 164 and EMR computer 50. The term "standalone" indicates that monitors 176 are not connected to network 100. Illustratively, standalone monitors 176 include a heart rate monitor 122', a respiration rate monitor 126', a blood pressure monitor 130', a pulse oximeter 134', and a temperature monitor 135. Other monitors 40' are depicted generically in FIG. 6 to indicate that other types of vital signs monitors or physiological parameter monitors (e.g., electroencephalographs (EEG's), weigh scales, capnographs, spirometers, etc.) may also be included in room 12 and may provide readings or measurements that are charted into the patient's EMR using dongle 164 of FIG. 6, or any of the other devices having voice-to-text module 46 as described above in connection with FIGS. 1-5 in other embodiments. Each of the standalone monitors 176 includes a display to permit the caregiver 20 to read the displayed measurement of the respective monitor 40', 122', 126', 130', 134', 135 aloud into dongle 64.

In the FIG. 6 embodiment, dongle 164 includes circuitry 172 that detects the presence of tag 28 of caregiver 20 in the respective room 12. In variant embodiments, the RTLS 24 of system 10 detects the presence of the tag 28 of caregiver 20 in the respective room as indicated (in phantom) in FIG. 6. In some such variant embodiments, circuitry 172 is omitted from dongle 172. In those embodiments in which RTLS 24 is used to detect the presence of the tag 28 of caregiver 20 in the room 12 with dongle 164, RTLS server 70 sends a message in this regard to EMR computer 50 in room 12, or else sends a message in this regard to EMR server 80 which, in turn, sends the message to EMR computer 50 in the room 12. In response to receiving the message regarding caregiver 20 presence in the room 12, the EMR computer 50 notifies dongle 164 via connector 168 and cable 166 and, in response to the notification from computer 50, voice-to-text module 46 of dongle 164 is activated to play the audible prompt through speaker 174 and to receive voice inputs through microphone 44.

In some embodiments, the patient room has some monitors 40 that are connected to network 100 (e.g., one or more of monitors 122, 126, 130, 134 of FIG. 5) and some standalone monitors 176 (e.g., one or more of monitors 122', 126', 130', 134', 135) that are not connected to network 100. In such embodiments, detection of caregiver tag 28 by circuitry 172 and/or RTLS 24 in the room 12 having dongle 164 connected to computer 50 results in the monitors 40 that are connected to the network automatically transmitting the vitals information via the network 100 to EMR server 80 for charting in the patient's EMR. The caregiver 20 then provides voice inputs into dongle 164 as described above to chart the vitals information (or other patient parameters) into the patient's EMR using dongle 164 along with any other clinical inputs the caregiver 20 may wish to chart into the patient's EMR.

To provide visual feedback to the caregiver 20 regarding the information that has been charted automatically into the patient's EMR, the EMR computer 50 of FIG. 6 displays a screen 138 like that shown in FIG. 5 with the automatically charted information populated into the respective fields 142, 146, 148, 150. The caregiver thereafter, is able to populate the blank fields 142, 146, 148, 150 corresponding to the standalone monitors 176 by providing voice inputs into dongle 164. The other clinical inputs fields 154, 156, 158, 160, 162 are also populated by voice inputs using dongle 164. Population of the blank fields 142, 146, 148, 150, 154, 156, 158, 160, 162 with the vocally input information indicates to the caregiver 20 that the populated information has also been input into the patient's EMR stored in EMR server 80.

In some embodiments, after the caregiver receives the audible prompt from the dongle 164, the caregiver provides voice inputs that include all of the vitals and other clinical inputs data that is to be stored in the patient's EMR in the EMR server 80 such as by saying all of the information to be input into the EMR back-to-back as one long voice input that is converted to one long string of text by module 46. In some such embodiments, the EMR server 80 parses subportions of the long string of text for storage in the patient's EMR based on keywords in the text. For example, the keywords may identify types of vital signs of the patient 18 that may be included in the text. In other embodiments, the parsing of the long string of text occurs at voice-to-text module 46 such that certain flags or codes are embedded in the string of text at certain locations to indicate the type of information at other locations in the long string of text. Alternatively or additionally, after parsing the long string of incoming voice input, either before or after converting the voice input to text, the voice-to-text module 46 transmits to EMR server 80 the discrete, parsed items of textual information corresponding to individual clinical inputs as separate data packets.

It is contemplated by this disclosure that the audible prompt from dongle 164 may include a series of audible prompts that request specific vital signs information be spoken by the caregiver 20 for input into the EMR of the respective patient 18 such that one piece of vital signs information is charted at a time in EMR server 80 before a subsequent audible prompt in the series is played through the speaker 174 of dongle 164. In some embodiments, the processor 56 is configured to determine whether a keyword is spoken by the caregiver to indicate that the specific vital signs information associated with the most recent audible prompt is not available for charting. In such instances, the processor 56 is configured to play the subsequent audible prompt in the series of audible prompts in response to determining that the keyword was spoken by the caregiver. Optionally, the series of audible prompts includes prompts for the caregiver 20 to verbally state one, two, or even more of the following vital signs of the patient: heart rate, respiration rate, blood pressure, oxygen saturation, or temperature.

In some embodiments, the instructions of the processor 56 of dongle 164, when executed, further results in one or more additional audible prompts being played through the speaker 174 after detection by the wireless communication circuitry 172 of the caregiver locating tag 28 in the patient room 12. For example, the one or more additional audible prompts may remind the caregiver 20 to populate the EMR of the patient 18 with clinical inputs relating to one or more conditions of the patient that do not correspond to vital signs of the patient. The clinical inputs may include information regarding one or more of the following: patient complexion, pain level of the patient, bruising of the patient, or any rashes on the patient, as has been mentioned above.

Optionally, the processor 56 of dongle 164 implements a delay time after detection of the caregiver 20 in the patient room 12 before any of the audible prompts is played through the speaker 174. In such embodiments, the processor 56 plays the one or more audible prompts through the speaker 174 after the delay time only if the wireless communication circuitry 172 still detects that the caregiver locating tag 28 is in the patient room 12. That is, the audible prompts are sounded only after module 46 of dongle 164 determines that the caregiver 20 intends to be in the room 12 for more than just a short period of time, such as about 10 seconds to about 30 seconds, for example.

Figure 7:
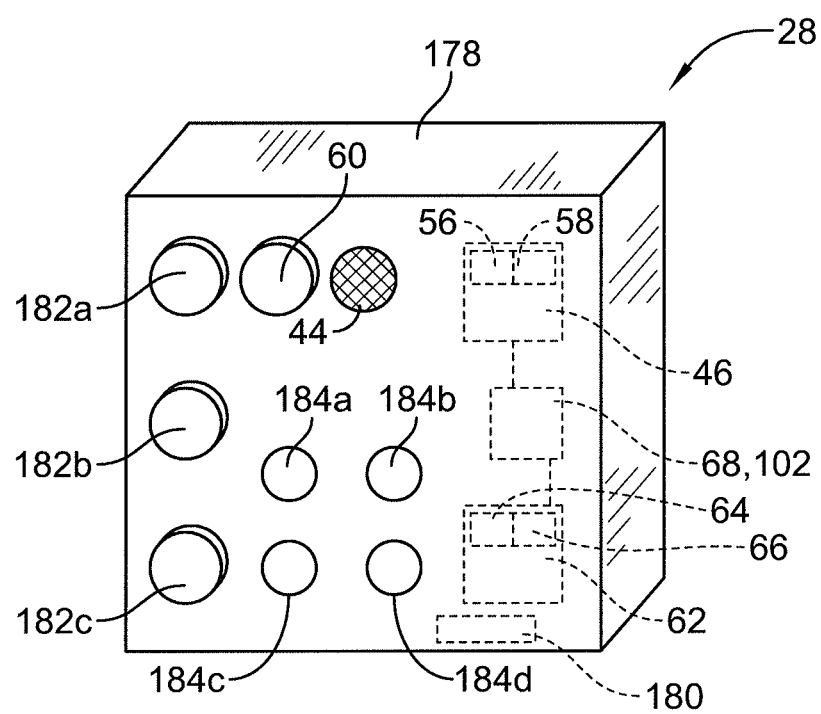
FIG. 7 is a perspective view of a caregiver location tag showing a transceiver (in phantom) and a battery (in phantom) within a tag housing, a microphone in the upper central region of the housing, a set of three caregiver activity buttons along a first side of the tag housing, each caregiver activity button being selected by the caregiver to transmit information regarding completion of a respective caregiver activity to an EMR system for charting in an electronic medical record of a patient associated with a patient room in which the caregiver is located at the time of pressing the respective caregiver activity button, and a set of four vitals charting buttons, each vitals charting button being selected by the caregiver to cause transmission of patient vital signs data from at least one piece of vital sign monitoring equipment to the EMR system for charting in the electronic medical record of the patient associated with the patient room in which the caregiver is located at the time of selection of the respective vitals charting button.

Referring now to FIG. 7, an alternative embodiment of caregiver location tag 28 includes a housing 178 having an interior region in which voice-to-text module 46 (in phantom) with its microprocessor 56 (in phantom) and memory 58 (in phantom) are situated along with tag circuitry 62 (in phantom) including its microprocessor 64 and memory 66 (in phantom). Communication circuitry 68, 102 (in phantom) is shown as a single block to indicate that tag 28 of FIG. 7 may include UWB communication circuitry 68 for wireless communication with UWB transceivers 26 of RTLS 23 or WiFi circuitry 102 for communication with one or more WAP's 52 or both. Thus, all information, including the text converted from voice my module 46, is transmitted from tag 28 of FIG. 7 by UWB communication circuitry 68 in embodiments of tag 28 that lack WiFi communication circuitry 102. Similarly, all information, including locating information, is transmitted from tag 28 of FIG. 7 by WiFi communication circuitry 102 in embodiments of tag 28 that lack UWB communication circuitry 68. The discussion above of tag 28 of FIG. 2 is equally applicable to tag 28 of FIG. 7 unless specifically noted otherwise. Thus, like reference numbers are used in FIGS. 2 and 7 to denote like components of tag 28 of the respective embodiments and variants thereof.

Still referring to FIG. 7, tag 28 includes one or more batteries 180 that are used to provide power to the electrical circuitry 46, 56, 58, 62, 64, 68, 102 of tag 28 and that, in some embodiments, are rechargeable batteries. Similar to some embodiments of tag 28 of FIG. 2, the tag 28 of FIG. 7 also has microphone 44 and button 60 which are electrically coupled to module 46 and operate in the same manner as described above in connection with FIG. 2. The main difference between tag 28 of FIG. 7 and tag 28 of FIG. 2, is that the tag 28 of FIG. 7 includes a first set of buttons 182a, 182b, 182c and a second set of buttons 184a, 184b, 184c, 184d. Each of buttons 182a, 182b, 182c, 184a, 184b, 184c, 184d is electrically coupled to module 46 or to circuitry 62 at the option of the tag designer. The first set of buttons 182a, 182*b*, 182*c* are caregiver activity buttons and the second set of buttons 184*a-d* are clinical input buttons.

For discussion purposes below, it will be assumed that buttons 182*a*, 182*b*, 182*c*, 184*a*, 184*b*, 184*c*, 184*d* are electrically coupled to circuitry 62 and that WiFi communication circuitry 102 is used to wirelessly transmit information regarding the use of buttons 182*a*, 182*b*, 182*c*, 184*a*, 184*b*, 184*c*, 184*d*. In other embodiments, buttons 182*a*, 182*b*, 182*c*, 184*a*, 184*b*, 184*c*, 184*d* are electrically coupled to module 46 and UWB communication circuitry 68 is used to wirelessly transmit information regarding the use of buttons 182*a*, 182*b*, 182*c*, 184*a*, 184*b*, 184*c*, 184*d*. In still other embodiments, some of buttons 182*a*, 182*b*, 182*c*, 184*a*, 184*b*, 184*c*, 184*d* are electrically coupled to module 46 and others of buttons 182*a*, 182*b*, 182*c*, 184*a*, 184*b*, 184*c*, 184*d* are electrically coupled to circuitry 62 and the associated communication circuitry 68, 102 is used to transmit information regarding the use of buttons 182*a*, 182*b*, 182*c*, 184*a*, 184*b*, 184*c*, 184*d*. For example, caregiver activity buttons 182*a*, 182*b*, 182*c* are electrically coupled to circuitry 62 and clinical input buttons 184*a*, 184*b*, 184*c*, 184*d* are electrically coupled to module 46 in some embodiments.

Each caregiver activity button 182*a*, 182*b*, 182*c* is selected by the caregiver 20 to signal circuitry 62 to transmit information regarding completion of a respective caregiver activity to EMR server 80 for charting in the EMR of the patient 18 associated with the patient room 12 in which the caregiver 20 is located at the time of pressing the respective caregiver activity button 182*a*, 182*b*, 182*c*. Each clinical inputs button 184*a*, 184*b*, 184*c*, 184*d* is selected by the caregiver 20 to cause transmission of patient vital signs data from at least one piece of vital sign monitoring equipment 40 to the EMR server 80 for charting in the EMR of the patient 18 associated with the patient room 12 in which the caregiver is located at the time of selection of the respective clinical inputs button 184*a*, 184*b*, 184*c*, 184*d*. Thus, in some embodiments, tag 28 notifies EMR server 80 via network 100 and/or RTLS 24 that the caregiver 20 has pressed one of buttons 184*a*, 184*b*, 184*c*, 184*d* and the EMR server 80 responds by querying the vital signs monitor 40 associated with the particular button 184*a*, 184*b*, 184*c*, 184*d* that was pressed so that the queried vital signs monitor 40 transmits the vitals information back to server 80 via network 100 for storage in the EMR of the associated patient 18.

Based on the foregoing discussion, it should be appreciated that the present disclosure contemplates that, in some embodiments, each button 184*a*, 184*b*, 184*c*, 184*d* corresponds to a particular type of vital signs monitor (e.g., HR monitor, RR monitor, SpO2 monitor, BP monitor, temperature monitor, or the like). It should also be appreciated that while illustrative tag 28 of FIG. 7 has four buttons 184*a*, 184*b*, 184*c*, 184*d*, other embodiments of tag 28 many include more than four clinical inputs buttons or less than four clinical inputs buttons. Clinical inputs buttons that are dedicated to charting information from particular vital signs monitors 40 are sometimes referred to herein as vitals charting buttons.

In some embodiments of tag 28 of FIG. 7, selection of one of vitals charting buttons 184*a*, 184*b*, 184*c*, 184*d* results in patient vital signs data from multiple pieces of vital sign monitoring equipment 40 being charted into the EMR of the patient 18. Thus, by pressing a single button, say button 184*a*, vitals data from two or more of the following: a heart rate monitor, a respiration rate monitor, a blood pressure monitor, a temperature monitor, or a pulse oximeter, is charted into the patient's EMR. Embodiments having only one vitals charting button 184*a* is contemplated, therefore, in which pressing button 184*a* results in vitals data from all network connected vital signs monitors 40 in the room 12 with tag 28 being charted into the respective patient's EMR.

As to caregiver activity buttons 182*a*, 182*b*, 182*c*, it is contemplated by this disclosure that each button 182*a*, 182*b*, 182*c* corresponds to at least one of the following: completion of caregiver rounds, completion of medication administration, completion of physical therapy, or taking of at least one vital sign, just to name a few examples. It should be appreciated, therefore, that while illustrative tag 28 of FIG. 7 has three buttons 182*a*, 182*b*, 182*c*, other embodiments of tag 28 many include more than three caregiver activity buttons or less than three caregiver activity buttons. Thus, in response to one of buttons 182*a*, 182*b*, 182*c* being pressed on tag 28 of FIG. 7, the processor 64 of circuitry 62 signals the wireless communication circuitry 102 to transmit to the network 100 information corresponding to the completion of the caregiver activity indicated by the selection of the respective button 182*a*, 182*b*, 182*c* for ultimate delivery to EMR server 80 for storage in the EMR of the patient in which tag 28 is located.

In some embodiments of tag 28 of FIG. 7, textual information or icons are provided on, or adjacent to, buttons 182*a*, 182*b*, 182*c*, 184*a*, 184*b*, 184*c*, 184*d* to indicate their respective functions. For example, a heart icon is used on or adjacent to one of buttons 184*a*, 184*b*, 184*c*, 184*d* to indicate that it is used to chart heart rate data to the patient's EMR and a lungs icon is used on or adjacent to another of buttons 184*a*, 184*b*, 184*c*, 184*d* to indicate that it is used to chart respiration rate data to the patient's EMR. If textual information is provided, it can be printed directly on housing 178 or on the buttons 184*a*, 184*b*, 184*c*, 184*d* or on a label that adheres to housing 178 or on the buttons 184*a*, 184*b*, 184*c*, 184*d*. Alternatively or additionally, textual information or icons can be embossed on housing 178 or buttons 184*a*, 184*b*, 184*c*, 184*d* to indicate the button functionality.

While badge 28 of FIG. 7 is configured to communicate with RTLS 24, it should be noted that, in some embodiments, the badge 28 may have additional functionality that enables the caregiver 20 to access certain areas of the healthcare facility 10. For example, the caregiver badge 28 permits the caregiver 20 to gain access to a pharmacy or to a medication cabinet in some embodiments. Thus, one of the caregiver activity buttons 182*a*, 182*b*, 182*c* is pressed to indicate medication retrieval from a pharmacy or medication cabinet in some embodiments.

In some embodiments, circuitry 62 of tag 28 is configured to communicate wirelessly with one or more of the vital signs monitors 40 using circuitry 102 without involving network 100. In other words, wireless communication is established directly between tag 28 and one or more vital signs monitors 40 in such embodiments. Accordingly, pressing each vitals charting button 184*a*, 184*b*, 184*c*, 184*d* results in a wireless notification from tag 28 to the vital signs monitor 40 associated with the pressed button 184*a*, 184*b*, 184*c*, 184*d* to initiate vitals data transmission from the vital signs monitor 40 to EMR server 80 via network 100 for storage in the corresponding patient's EMR.

It is contemplated by this disclosure that each press or selection of any of button 182*a*, 182*b*, 182*c*, 184*a*, 184*b*, 184*c*, 184*d* is time stamped and recorded in the EMR of the associated patient 18 in the room in which the respective tag 28 is located. In some embodiments, tag 28 of FIG. 7 also includes a speaker, similar to speaker 174 of dongle 164, coupled to module 46 or circuitry 62. The speaker in tag 28 is used to provide audible prompts to the caregiver 20 regarding various clinical data that is to be recorded in the EMR of the respective patient. For example, on rounds, the caregiver 20 may be required to take the patient's temperature and monitor the patient's skin complexion. In response to entering the patient room 12 with tag 28 of FIG. 7 and/or in response to pressing any of buttons 60, 182*a*, 182*b*, 182*c*, 184*a*, 184*b*, 184*c*, 184*d*, the one or more audible prompts are played through the speaker to alert the caregiver 20 of the clinical inputs data, including vitals data, that the caregiver 20 should chart to the EMR for the particular patient 18.

Embodiments of tags 28 and dongle 164 are disclosed herein as including a speaker, such as speaker 174 of FIG. 6, that is coupled to voice-to-text module 46 and that is used to sound audible prompts to remind the caregiver to perform EMR charting tasks. It is contemplated by this disclosure that embodiments of patient support apparatus 14, computer 42, computer 50 in patient room 12, and audio station 54 also include a speaker coupled to the respective voice-to-text module 46 for sounding audible prompts similar to those discussed above in connection with dongle 164 of FIG. 6 and tag 28 of FIG. 7.

In the various examples depicted in FIGS. 1-4 and 7, voice-to-text module 46 is shown as a separate hardware component (e.g., a separate circuit board) within the device in which it is included. For example, FIGS. 2 and 7 illustrate module 46 as a hardware component separate from tag circuitry 62, FIG. 3 illustrates module 46 as a hardware component separate from bed circuitry 104, FIG. 4 illustrates module 46 as a hardware component separate from audio station circuitry 112. However, in other embodiments, voice-to-text module is implemented as voice-to-text software resident in the memory of the circuitry of the device in which it is included. For example, memory 66 of the various embodiments of tags 28 disclosed herein stores the software that implements the respective voice-to-text module, memory of bed circuitry 104 stores the software that implements the respective voice-to-text module, and memory 116 of audio station circuitry 112 stores the software that implements the respective voice-to-text module. Devices such as tag 28, patient support apparatus (e.g., bed) 14, computers 42, 50, audio station 54, and dongle 164 having microphone 44 and voice-to-text module 46 (hardware and/or software) are considered to be within the scope of the term "communication device" or "communication devices" herein.

This disclosure uses the term "server" to refer to computing devices that have the requisite processing power, computer memory, and other computer components to execute computer-executable instructions to accomplish the features described herein. Each such device may comprise one or multiple microprocessors, microcontrollers, or similar devices, or may comprise one or multiple servers that are linked via a communication network. Thus, servers are computers in some embodiments. Accordingly, an EMR computer having the requisite functionality may be configured as an EMR server, and vice versa. The same goes for nurse call computers and nurse call servers and for UWB hub computers and UWB RTLS servers (or RTLS computer and RTLS servers, in general).

The terms "information" and "data" are used interchangeably herein. Thus, information is considered to be within the scope of the term data and vice versa. The phrase "text data" and "text information" as well as just "text" are also used interchangeably herein. That is "text" and "text data" and "text information" are considered to be synonymous with each other herein. Furthermore, the phrases "vital signs data," "vital signs information," "vitals data," "vitals information," and "vitals" are used interchangeably and so are considered to be synonymous with each other herein.

Although this disclosure refers to specific embodiments, it will be understood by those skilled in the art that various changes in form and detail may be made without departing from the subject matter set forth in the accompanying claims.

The invention claimed is:

1. A charting system for a healthcare facility, the charting system comprising:
   a patient bed to support a patient in a patient room,
   a vital sign monitor configured to read at least one vital sign from the patient,
   an electronic medical record (EMR) computer communicatively coupled to the vital sign monitor, and
   a high accuracy locating system communicatively coupled to the vital sign monitor, the high accuracy locating system including locating transceivers situated throughout the healthcare facility and a caregiver locating tag worn by a caregiver, the caregiver locating tag communicating with one or more of the locating transceivers that are in communicative proximity with the caregiver locating tag, the locating system further including a locating server communicatively coupled to the locating transceivers and operable to determine a location of the caregiver locating tag in the healthcare facility within three feet or less of an actual location of the caregiver locating tag, the locating server being configured to send a first message to the vital sign monitor to start reading the at least one vital sign from the patient in response to detection that the caregiver locating tag has entered the patient room, the locating server being configured to send a second message to the vital sign monitor to transmit vital sign information as read by the vital sign monitor to the EMR computer in response to detection that the caregiver locating tag is within a threshold distance of the patient bed.

2. The charting system of claim 1, wherein the plurality of transceivers communicates via ultra-wideband (UWB) signals with the caregiver locating tag.

3. The charting system of claim 2, wherein the location of the caregiver locating tag is determined by the locating server using two way ranging and time difference of arrival (TDOA) techniques.

4. The charting system of claim 2, wherein the locating server uses signals from only a subset of the plurality of transceivers to determine the location of the caregiver locating tag, the subset being determined based on signal strength of signals between the caregiver locating tag and the plurality of transceivers.

5. The charting system of claim 4, wherein the subset comprises at least three transceivers from the plurality of transceivers having highest signal strength values as compared to others of the plurality of transceivers.

6. The charting system of claim 1, wherein the high accuracy locating system includes an equipment locating tag attached to the patient bed and in communication with the plurality of transceivers, wherein the locating server of the high accuracy locating system is operable to determine a location of the equipment locating tag in the healthcare facility within three feet or less of an actual location of the equipment locating tag, and wherein the threshold distance between the caregiver locating tag and the patient bed is determined based on a tag distance between the caregiver locating tag and the equipment locating tag.

7. The charting system of claim 1, further comprising a microphone configured to receive voice inputs from a caregiver.

8. The charting system of claim 7, wherein the microphone is included as part of the patient bed located in a patient room.

9. The charting system of claim 7, wherein the microphone is included as part of the caregiver locating tag.

10. The charting system of claim 7, further comprising an audio station of a nurse call system, the audio station being located in the patient room, and the microphone being included in the audio station.

11. The charting system of claim 7, further comprising a computer located in the patient room and a dongle coupled to the computer, and wherein the microphone is included in the dongle.

12. The charting system of claim 7, wherein words spoken by the caregiver and received by the microphone are converted to text by a voice-to-text module and transmitted for receipt by the EMR computer.

13. The charting system of claim 12, wherein the voice-to-text module is configured to be activated with a button.

14. The charting system of claim 12, wherein the voice-to-text module is configured to be activated in response to the caregiver speaking a keyword.

15. The charting system of claim 12, wherein the voice-to-text module is configured to be activated in response to the caregiver entering the patient room.

16. The charting system of claim 12, wherein the voice-to-text module is configured to be activated in response to the caregiver locating tag being within a predetermined distance of a device.

17. The charting system of claim 16, wherein the device comprises the patient bed or the vital sign monitor.

18. The charting system of claim 1, wherein the caregiver locating tag includes a plurality of buttons, each button of the plurality of buttons being related to a respective caregiver activity, each button of the plurality of buttons being selectable by the caregiver to convey information about the respective caregiver activity to the EMR computer.

19. The charting system of claim 18, wherein the respective caregiver activity for at least one of the buttons of the plurality of buttons includes at least one of the following: completion of caregiver rounds, medication administration, completion of physical therapy, or taking of the at least one vital sign.

20. The charting system of claim 1, further comprising a remote computer communicatively coupled to the vital sign monitor and wherein the vital sign monitor is configured to initiate transmission of the at least one vital sign to the remote computer such that the at least one vital sign is sent to both the EMR computer and the remote computer.

* * * * *